US 7,819,926 B1

(12) United States Patent
Longino

(10) Patent No.: US 7,819,926 B1
(45) Date of Patent: Oct. 26, 2010

(54) PROSTHETIC FOOT AND ANKLE

(76) Inventor: Keith Longino, 4805 Mendota Ave., Los Angeles, CA (US) 90042

( * ) Notice: Subject to any disclaimer, the term of this patent is extended or adjusted under 35 U.S.C. 154(b) by 0 days.

(21) Appl. No.: 12/231,107

(22) Filed: Aug. 29, 2008

Related U.S. Application Data

(60) Provisional application No. 60/966,884, filed on Aug. 29, 2007.

(51) Int. Cl.
A61F 2/64 (2006.01)
A61F 2/66 (2006.01)

(52) U.S. Cl. .......................... 623/47; 623/53
(58) Field of Classification Search .............. 623/47–56
See application file for complete search history.

(56) References Cited

U.S. PATENT DOCUMENTS

| 78,048 | A | * | 5/1868 | Briody ................. 623/50 |
|---|---|---|---|---|
| 3,889,300 | A | | 6/1975 | Smith |
| 3,982,280 | A | | 9/1976 | Asbelle et al. |
| 3,987,500 | A | | 10/1976 | Schlein |
| 4,306,320 | A | | 12/1981 | Delp |
| 4,360,931 | A | | 11/1982 | Hampton |
| 4,446,580 | A | | 5/1984 | Furuya et al. |
| 4,636,220 | A | | 1/1987 | Ziegelmeyer |
| 4,645,509 | A | | 2/1987 | Poggi et al. |
| 4,865,612 | A | | 9/1989 | Arbogast et al. |
| 4,892,554 | A | | 1/1990 | Robinson |
| 5,037,444 | A | | 8/1991 | Phillips |
| 5,062,859 | A | | 11/1991 | Naeder |
| 5,116,384 | A | | 5/1992 | Wilson et al. |
| 5,139,525 | A | | 8/1992 | Kristinsson |
| 5,156,632 | A | | 10/1992 | Wellershaus |
| 5,158,570 | A | | 10/1992 | Schey et al. |
| 5,219,365 | A | | 6/1993 | Sabolich |
| 5,258,038 | A | | 11/1993 | Robinson |
| 5,326,365 | A | | 7/1994 | Alvine |
| 5,443,527 | A | | 8/1995 | Wilson |
| 5,683,468 | A | | 11/1997 | Pappas |
| 5,695,526 | A | | 12/1997 | Wilson |
| 5,728,177 | A | | 3/1998 | Phillips |
| 5,769,896 | A | | 6/1998 | Rosendahl et al. |
| 5,913,902 | A | | 6/1999 | Geible |
| 6,120,547 | A | | 9/2000 | Christensen |
| 6,129,766 | A | | 10/2000 | Johnson et al. |
| 6,187,052 | B1 | | 2/2001 | Molino |
| 6,290,730 | B1 | | 9/2001 | Pitkin et al. |
| 6,443,995 | B1 | | 9/2002 | Townsend et al. |

(Continued)

OTHER PUBLICATIONS www.apcomponents.com; American Prosthetic Components, Inc.; DuroFlex.

Primary Examiner—William H Matthews
Assistant Examiner—Marcia Hoffman
(74) Attorney, Agent, or Firm—Patent Law Agency, LLC; Peter Ganjian

(57) ABSTRACT

The present invention discloses a prosthetic foot and ankle, comprising an ankle assembly coupled with a foot assembly by an arch suspension yoke, with the ankle assembly enabling primary articulations of the foot assembly and the pre-orientation thereof in relation to a vertical axis. Further, the foot assembly having a plantar surface and a dorsal surface includes a heel coupled with a fore foot by the arch suspension yoke, with the arch suspension yoke enabling secondary articulations of the foot assembly. Prosthetic foot and ankle further includes leaf springs and elastomer springs enabling tertiary articulations throughout the prosthetic foot and ankle.

18 Claims, 40 Drawing Sheets

U.S. PATENT DOCUMENTS

| | | |
|---|---|---|
| 6,719,807 B2 | 4/2004 | Harris |
| 6,733,984 B2 | 5/2004 | Jenkins |
| 6,793,683 B1 * | 9/2004 | Laghi .......................... 623/52 |
| 6,926,739 B1 | 8/2005 | O'Connor et al. |
| 2004/0186585 A1 | 9/2004 | Feiwell |
| 2005/0182492 A1 | 8/2005 | Pappas et al. |
| 2006/0020345 A1 | 1/2006 | O'Connor et al. |
| 2007/0106396 A1 | 5/2007 | Doddroe et al. |

* cited by examiner

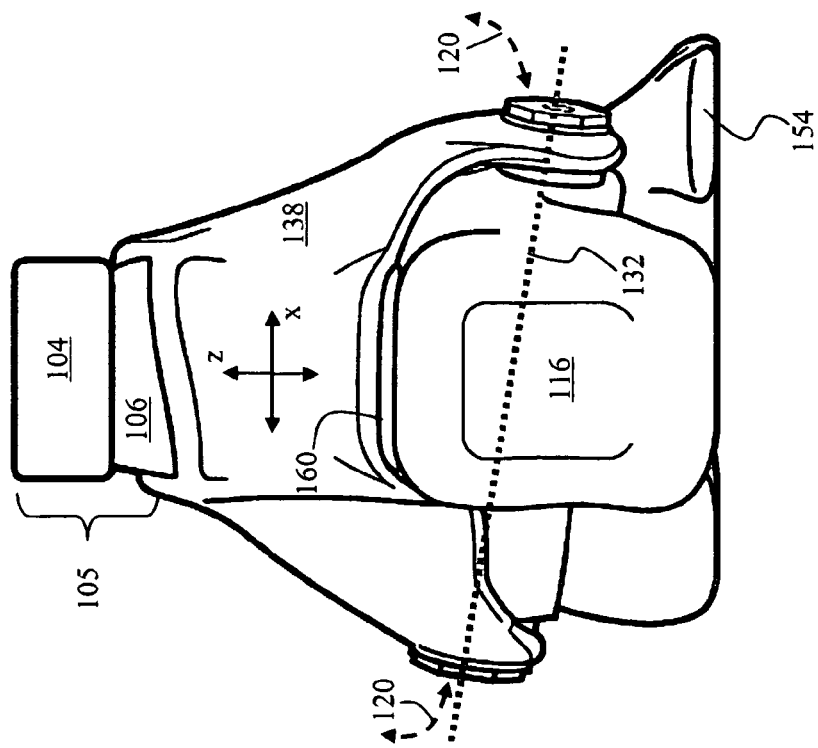
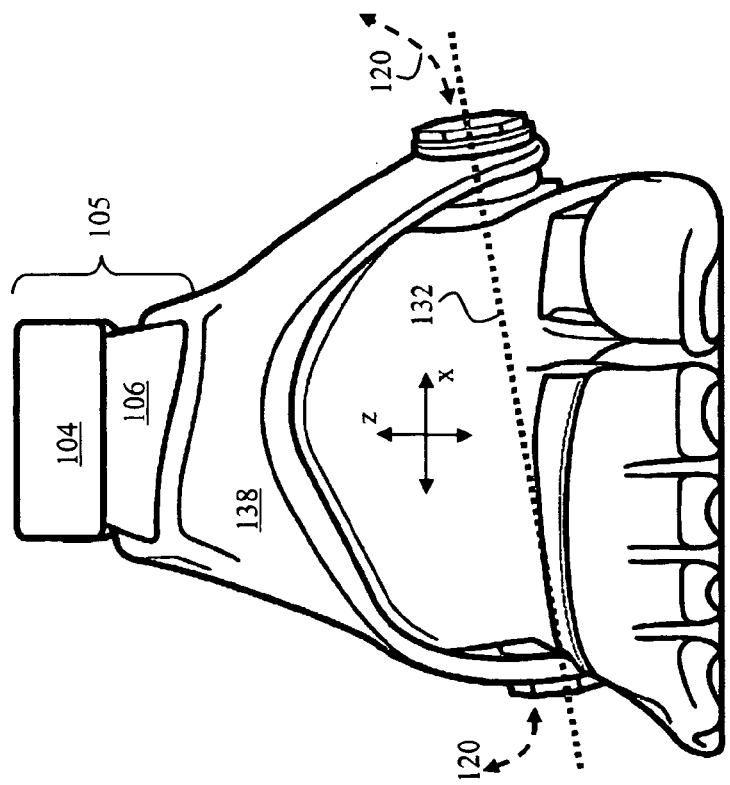
FIG. 1D
FIG. 1C

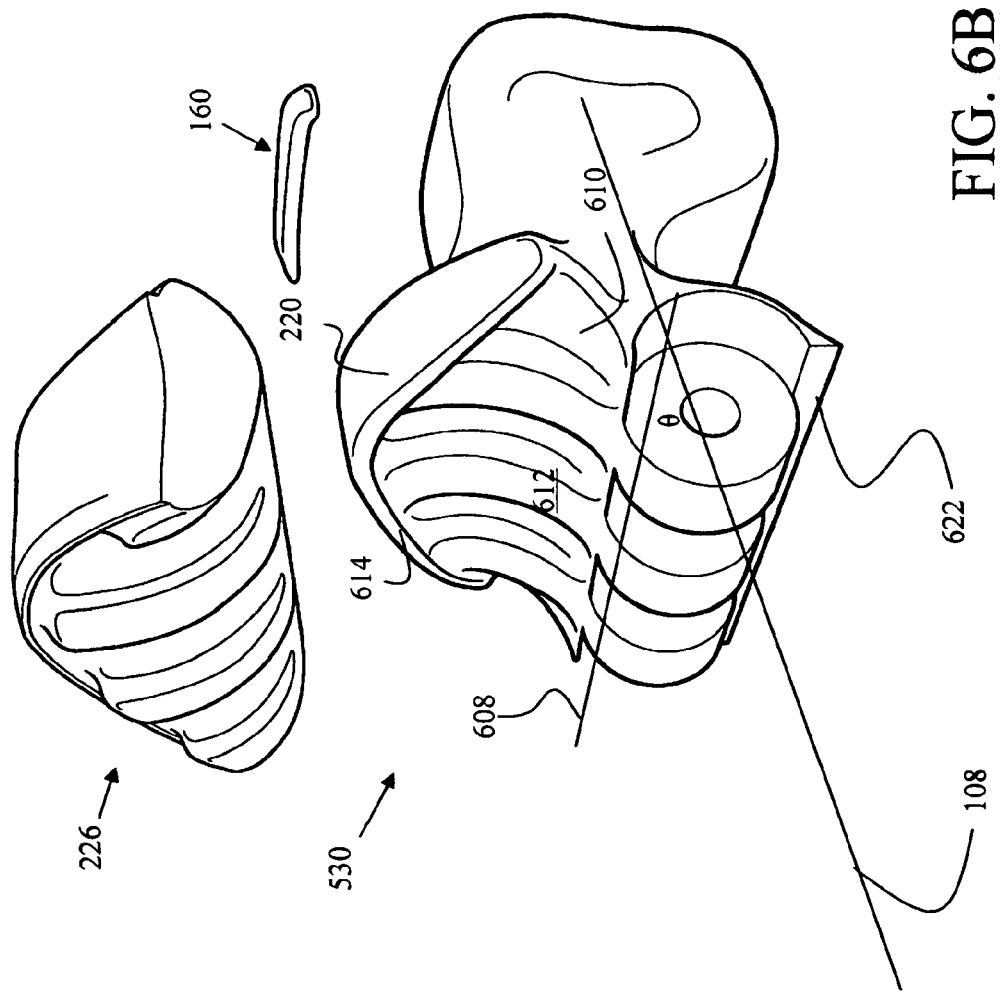

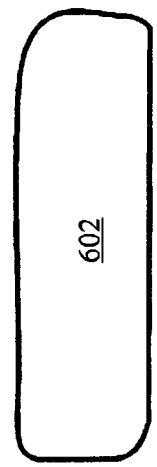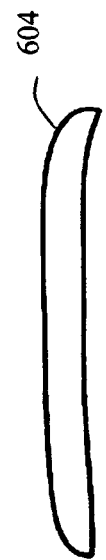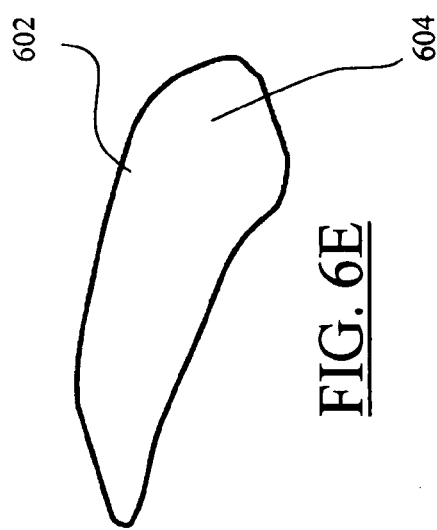

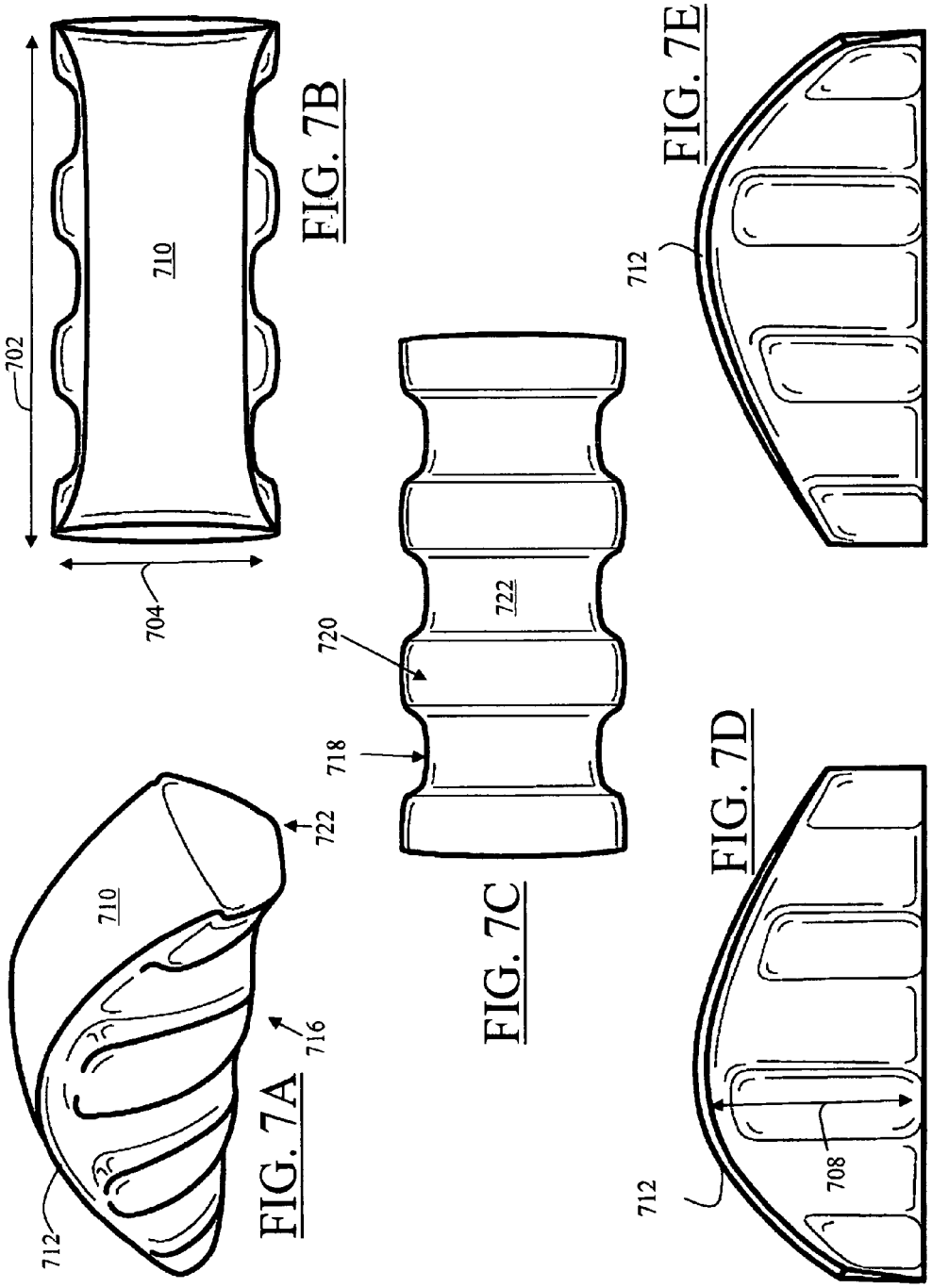

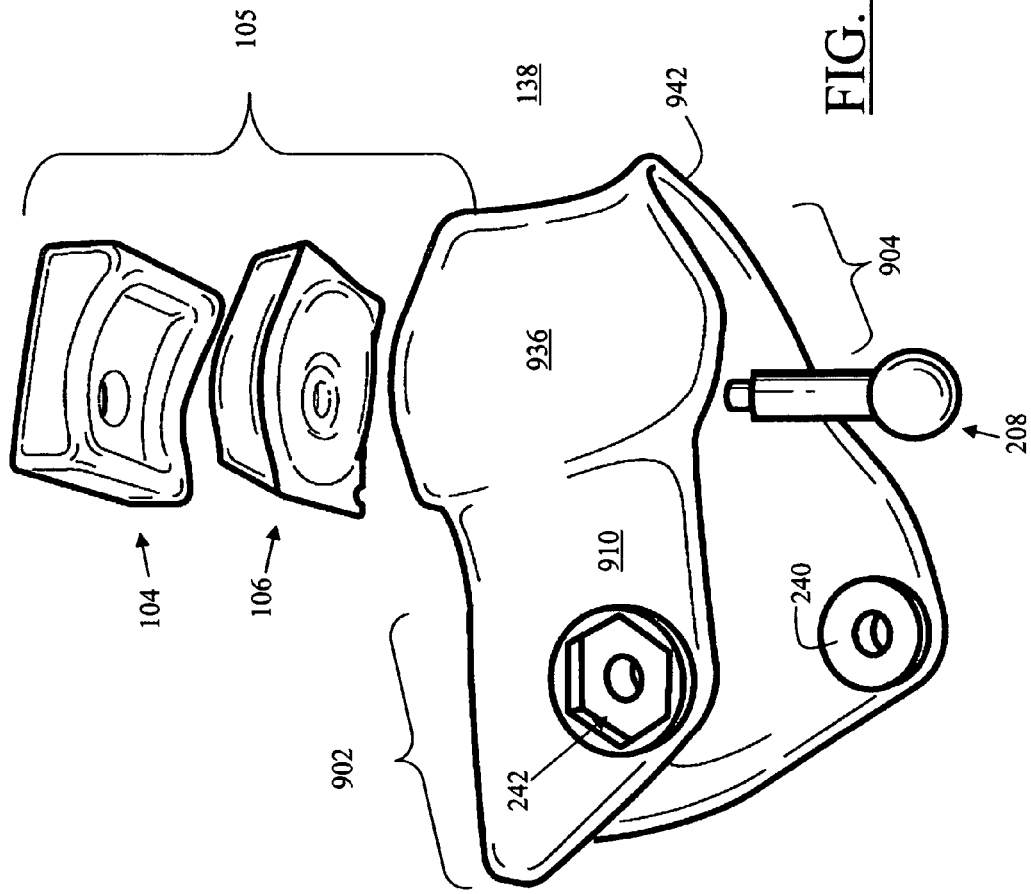

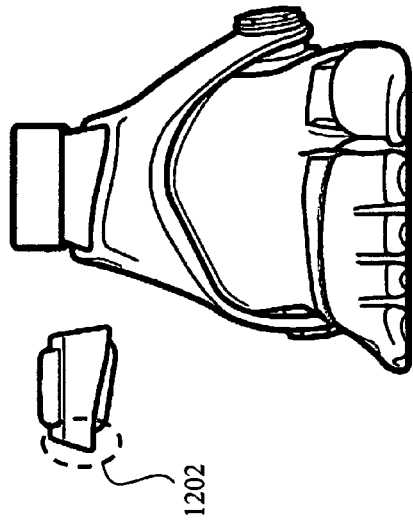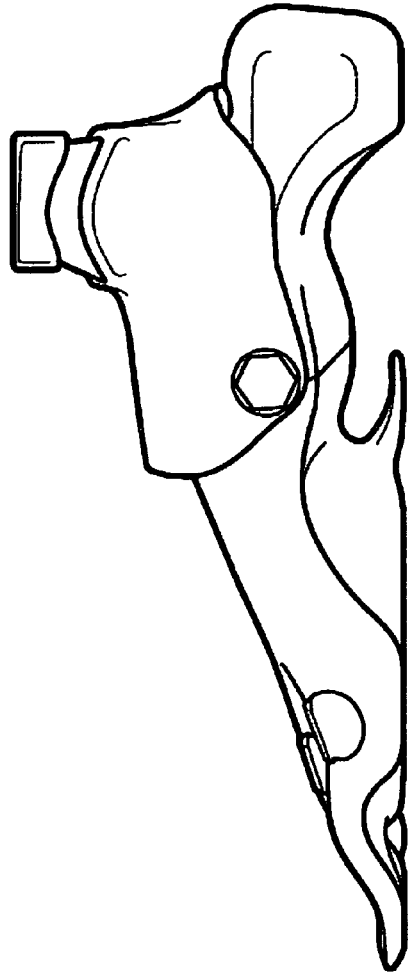
FIG. 12A
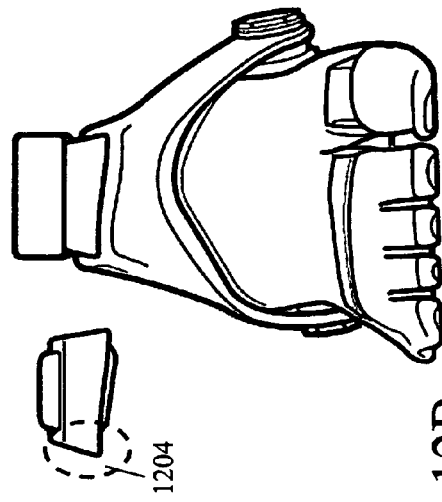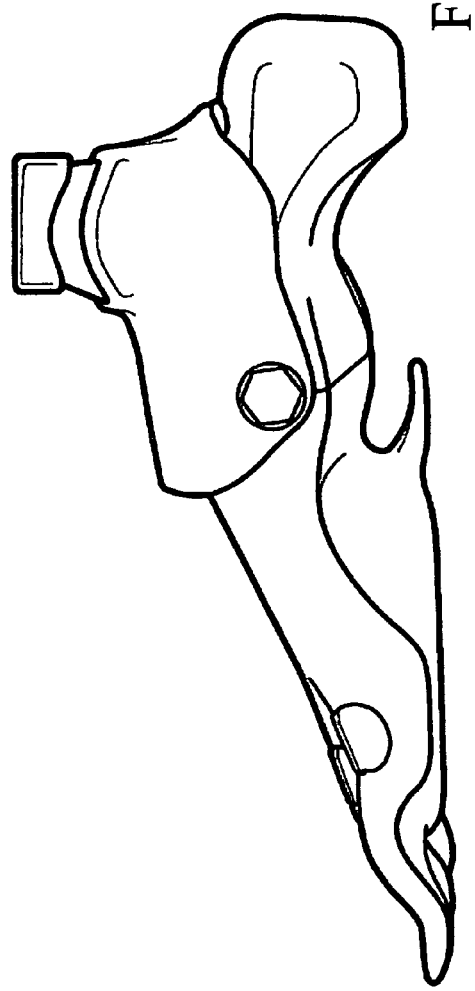
FIG. 12B

PROSTHETIC FOOT AND ANKLE

CROSS-REFERENCE TO RELATED APPLICATIONS

This Application claims the benefit of priority of co-pending U.S. Utility Provisional Patent Application No. 60/966,884 filed Aug. 29, 2007, the entire disclosure of which application is expressly incorporated by reference in its entirety herein.

BACKGROUND OF THE INVENTION

1. Field of the Invention

This invention relates to a prosthetic foot and ankle and, more particularly, to a prosthetic foot and ankle with asymmetrically cascading motion and incremental articulations that closely mimic the natural motion of a human foot and ankle.

2. Description of Related Art

Conventional prosthetic devices are well known and have been in use for a number of years. Reference is made to the following few exemplary U.S. Patent Publications, including U.S. Pat. Nos. 5,326,365; 5,443,527; 5,116,384; 3,982,280; 5,158,570; 5,728,177; 6,926,739; 3,889,300; 3,987,500; 6,733,260; 6,290,730; 5,683,468; 5,913,902; 4,360,931; 5,258,038; 4,645,509; 4,892,544; 5,037,444; 5,156,632; 4,636,220; 5,062,859; 4,865,612; 4,306,320; 5,219,365; 5,139,525; 4,446,580; 6,129,766; 6,443,995; 5,695,526; 6,120,547; 5,769,896; 5,443,527; 6,187,052; 6,719,807; and U.S. Patent Application Publications 2007/0106396; 2006/0020345; 2005/0182492; 2004/0186585. Regrettably, most prior art conventional prosthetic devices suffer from obvious disadvantages in that they are bulky and do not simulate the natural motion of the human extremity such as a human ankle and foot.

Accordingly, in light of the current state of the art and the drawbacks to current prosthetic devices mentioned above, a need exists for a prosthetic device that closely resembles the anatomy of the human body extremity in terms of structure (e.g., ankle and foot), and closely mimics the natural motion of a human extremity such as the ankle and foot.

BRIEF SUMMARY OF THE INVENTION

The present invention provides a prosthetic foot and ankle, comprising:
an ankle assembly coupled with a foot assembly, with the ankle assembly enabling primary articulations of the foot;
the foot assembly having a plantar surface and a dorsal surface includes a heel coupled with a fore foot by an arch suspension yoke, with the arch suspension yoke enabling secondary articulations of the foot assembly.

An exemplary optional aspect of the present invention provides a prosthetic foot and ankle, wherein:
the primary articulations are comprised of motions of dorsiflexion and planiflexion, inversion and eversion, and transverse rotation.

Another exemplary optional aspect of the present invention provides a prosthetic foot and ankle, wherein:
the secondary articulations are comprised of an arch flex motion about an arch flex pivot axis, which enable fore foot proximal end and a heel proximal end to travel in a reciprocal arc defined by the arch flex pivot axis.

Yet another exemplary optional aspect of the present invention provides a prosthetic foot and ankle, wherein:

the fore foot includes:
a primary section configured as phalanges;
a secondary section configures as metatarsal joints;
a tertiary section configured as metatarsals; and
a quaternary section for coupling the fore foot with the heel, arch suspension yoke, and the ankle assembly.

Still another exemplary optional aspect of the present invention provides a prosthetic foot and ankle, wherein:
the primary section of the fore foot includes individually separate:
a first toe, a second toe, a third toe, a fourth toe, and a fifth toe, with each toe comprising:
a single piece unit having dorsal and plantar surfaces with substantially flat toe distal end continued obliquely to a raised toe median section that ends at a toe proximal end, with the toe median section forming a toe leaf spring enabling individual, tertiary articulations of the first toe, the second toe, the third toe, the fourth toe, and the fifth toe.

A further exemplary optional aspect of the present invention provides a prosthetic foot and ankle, wherein:
the primary section of the fore foot further includes an abbreviated interosseous space between the first toe and the second toe.

Still a further exemplary optional aspect of the present invention provides a prosthetic foot and ankle, wherein:
the secondary section of the fore foot includes:
a first biasing mechanism with a first axial length and a second biasing mechanism with a second axial length that is longer than the first axial length; the first axial length is oriented substantially transverse the longitudinal axis of the foot assembly, and the second axial length is oriented at an angle $\psi$ the longitudinal axis of the foot assembly;
the first and the second biasing mechanisms are substantially cylindrical;
the first biasing mechanism is positioned slightly posterior the second biasing mechanism, with the first and second biasing mechanisms having a center line axis that is slightly bent;
the first biasing mechanism and the second biasing mechanism comprising:
a substantially "C" shaped toe spring cavity for housing a spring, including a joint leaf spring at a bottom surface of the toe spring cavity;
the toe spring cavity includes:
an elongated canal with a plurality of flanges, the flanges are aligned laterally along an axial width of the toe spring cavity, forming an alternating protuberance and depression within the toe spring cavity;
dorsal, inner bottom surface of the toe spring cavity is smooth and concaved, with the plantar, outer surface substantially flat, forming the joint leaf spring;
the spring is comprised of:
an elastomer having an axial length, a width, and a thickness;
a top surface that includes slightly convex section that is extended longitudinally, along the axial length L of the spring;
the slightly convex section includes lateral edge depressions extending longitudinally, along the axial length L of the spring;
two lateral side surfaces, and extending longitudinally along the axial length L of the spring;
the lateral side surfaces include a plurality of notches that are formed into the lateral side surfaces of the spring;

the notches are aligned laterally along the axial length L of the spring, forming an alternating notch and protuberance;

each notch of the plurality of notches is comprised of a substantially flat base, with the perpendicular protuberances forming two side walls of each notch; and a bottom surface;

the spring having the plurality of notches, positioned laterally along an axial length of the spring, with each notch biased against a corresponding protrusion on the spring cavity;

the spring contacting the spring cavity and biasing the spring cavity so that the spring cavity counter-rotates about the center line axis of the first and the second biasing mechanisms.

Another exemplary optional aspect of the present invention provides a prosthetic foot and ankle, wherein:

the tertiary section configured as metatarsals, includes:

oblique, dorsal surface forming an asymmetrical convex configuration extending transversely, oriented parallel a width of the foot from an inner side of foot to an outer side of the foot;

a balancing protuberance in the outer side of the foot extending parallel along longitudinal axis of the foot proximal a first pivot axis, including a balancing leaf spring; and a fore foot main arch at the inner side of the foot.

Yet another exemplary optional aspect of the present invention provides a prosthetic foot and ankle, wherein:

the quaternary section includes a first section of a hinge biasing mechanism having a longitudinal axis oriented at an angle θ to the longitudinal axis of the foot assembly, and tilted down at an angle φ from an inner fore foot to the outer fore foot;

the first section of the hinge foot biasing mechanism further comprising:

fore foot hinge barrels, oriented transverse the longitudinal axis of the foot;

the fore foot hinge barrels are comprised of integrally circular, hollow sections forming a set of fore foot pivot knuckles of a main hinge;

the set of fore foot pivot knuckles are inserted and interlocked with a set of heel pivot knuckles, with the integrally circular, hollow sections of the set of fore foot pivot knuckles and the heel pivot knuckles aligned, through which a main pin is inserted coupling the set of fore foot pivot knuckles and the heel pivot knuckles, forming the main hinge;

the first section of the hinge biasing mechanism includes a first section wall, having a plurality of vertically oriented flanges with smooth, rounded surfaces that are aligned laterally along the first section wall;

the first section of the hinge biasing mechanism also includes a first section top having a length that extends longitudinally along an axial width of the foot assembly and has a width forming a first lip;

a first top surface of a spring includes a first lateral edge depression that securely abuts the first lip of the first section of the hinge biasing mechanism.

Still another exemplary optional aspect of the present invention provides a prosthetic foot and ankle, wherein:

the heel is comprised of:

a posterior heel section with part of the dorsal surface covered with a heel damper mechanism;

a heel arch; and a second section of a hinge biasing mechanism.

A further exemplary optional aspect of the present invention provides a prosthetic foot and ankle, wherein:

the heel damper is comprised of an elastomer.

Still a further exemplary optional aspect of the present invention provides a prosthetic foot and ankle, wherein:

the second section of a hinge biasing mechanism has a longitudinal axis oriented at an angle θ to the longitudinal axis of the foot assembly, and tilted down at an angle φ from an inner fore foot to an outer fore foot, and comprising:

heel hinge barrels, oriented transverse the longitudinal axis of the foot;

the heel hinge barrels are comprised of integrally circular, hollow sections forming a set of heel pivot knuckles of a main hinge;

the set of heel pivot knuckles are inserted and interlocked with a set of fore foot pivot knuckles, with the integrally circular, hollow sections of the set of fore foot pivot knuckles and the heel pivot knuckles aligned, through which a main pin is inserted coupling the set of fore foot pivot knuckles and the heel pivot knuckles, forming the main hinge;

the second section of the hinge biasing mechanism includes a second section wall, having a plurality of vertically oriented flanges with smooth, rounded surfaces that are aligned laterally along the second section wall;

the second section of the hinge biasing mechanism also includes a second section top having a length that extends longitudinally along an axial width of the foot assembly and has a width forming a second lip;

a first top surface of a spring includes a second lateral edge depression that securely abuts the second lip of the second section of the heel-fore foot biasing mechanism.

Yet a further exemplary optional aspect of the present invention provides a prosthetic foot and ankle, wherein:

the arch suspension yoke includes:

an asymmetrical anterior section;

an asymmetrical medial section; and an asymmetrical posterior section.

Another exemplary optional aspect of the present invention provides a prosthetic foot and ankle, wherein:

the asymmetrical anterior section includes:

a substantially saddle shaped dorsal surface with asymmetrical anterior lateral walls;

a first stop integral with bottom surface of a first distal end of the anterior section, limiting the secondary articulations of the fore foot in the dorsiflexion and planiflexion motions;

a main hinge coupler for coupling the fore foot, the heel and the arch suspension yoke along an arch flex pivot axis;

the main hinge is comprised of a first main hinge coupler facing an outer foot, which is positioned lower than a second main hinge coupler facing an inner foot, with the first main hinge coupler and the second hinge coupler aligned along the arch flex pivot axis.

Yet another exemplary optional aspect of the present invention provides a prosthetic foot and ankle, wherein:

the asymmetrical medial section includes:

a second stop integral with bottom surface of a medial section, limiting the secondary articulations of the fore foot in the dorsiflexion and planiflexion motions;

a shaft aperture axially aligned with a leg for insertion of a ball joint shaft for coupling of the arch suspension yoke with the ankle assembly;

a top surface of the medial section includes asymmetrical, substantially rectangular housing formed from protruded perimeter edges, which house an ankle elastomer, with an asymmetrical interior bottom surface;

the protruded perimeter edges and the interior bottom surface along an outer foot assembly is higher than the protruded perimeter edges and the interior bottom surface along an inner foot assembly, limiting and directing primary articulations;

the top surface further includes a dome wall surrounding the shaft aperture, constituting the ball joint shaft capture;

medial lateral walls include substantially vertically oriented incurvate section on the inner foot assembly side, and substantially convex on the outer foot side.

Still, another exemplary optional aspect of the present invention provides a prosthetic foot and ankle, wherein:

the asymmetrical posterior section includes:

a posterior, vertically oriented wall with an incurvate at a mid-section having a concaved portion that is substantially parallel with the transverse direction of the foot;

a third stop integral with bottom surface of posterior section, limiting the secondary and tertiary articulations of the heel when in contact with a heel damper elastomer.

A further exemplary optional aspect of the present invention provides a prosthetic foot and ankle, wherein:

the ankle assembly is comprised of:

an asymmetrical fastener element having a threaded shaft hole axially aligned with a shaft aperture of the arch suspension yoke for insertion of a ball joint shaft for coupling of the arch suspension yoke with the fastener element to form the ankle assembly;

the asymmetrical fastener element having:

a lateral perimeter that is configured substantially rectangular with a length that is substantially parallel with a length of the foot assembly and a width that is transverse the length, and an anterior height that is shorter than a posterior height;

a substantially flat fixation surface;

a bottom surface cavity for housing an ankle spring;

bottom surface rim, protruded form the lateral perimeter and extending along the bottom surface perimeter, with a length side concaved and a width sides flat, inversely commensurate with a top surface of a medial section of the arch suspension yoke.

Yet a further exemplary optional aspect of the present invention provides a prosthetic foot and ankle, wherein:

the plantar surface of the foot assembly includes:

a fore-foot planter surface, comprising:

a primary section configured as phalanges;

a secondary section configures as metatarsal joints;

a tertiary section configured as metatarsals; and a quaternary section for coupling the fore foot with the heel, arch suspension yoke, and the ankle assembly; and a heel planter surface comprising:

a second section of a hinge biasing mechanism;

a heel arch; and posterior planter surface of the heel.

Another exemplary optional aspect of the present invention provides a prosthetic foot and ankle, wherein:

a ball joint shaft that couples the arch suspension yoke with a fastener element, forming the ankle assembly.

These and other features, aspects, and advantages of the invention will be apparent to those skilled in the art from the following detailed description of preferred non-limiting exemplary embodiments, taken together with the drawings and the claims that follow.

BRIEF DESCRIPTION OF THE DRAWINGS

It is to be understood that the drawings are to be used for the purposes of exemplary illustration only and not as a definition of the limits of the invention. Throughout the disclosure, the word "exemplary" is used exclusively to mean "serving as an example, instance, or illustration." Any embodiment described as "exemplary" is not necessarily to be construed as preferred or advantageous over other embodiments.

Referring to the drawings in which like reference character(s) present corresponding part(s) throughout:

FIG. 1C is an exemplary plan frontal view of the prosthetic extremity of FIG. 1A;

FIG. 1D is an exemplary plan back view of the prosthetic extremity of FIG. 1A;

FIG. 6B is an exemplary exploded perspective view of the proximal end of the heel of the prosthetic extremity of FIG. 1A;

FIGS. 6E to 6G are exemplary perspective views of the damper of the heel of the prosthetic extremity of FIG. 1A;

FIGS. 7A to 7E are exemplary views of the third elastomer spring of the prosthetic extremity of FIG. 1A;

FIGS. 9A to 9G are exemplary views of the arch suspension yoke of the prosthetic extremity of FIG. 1A;

FIGS. 12A and 12B are exemplary views of the effects on the prosthetic foot when varying the dimensions of the fourth elastomer spring of the prosthetic extremity of FIG. 1A.

DETAILED DESCRIPTION OF THE INVENTION

The detailed description set forth below in connection with the appended drawings is intended as a description of presently preferred embodiments of the invention and is not intended to represent the only forms in which the present invention may be constructed and or utilized.

Figure 1A:
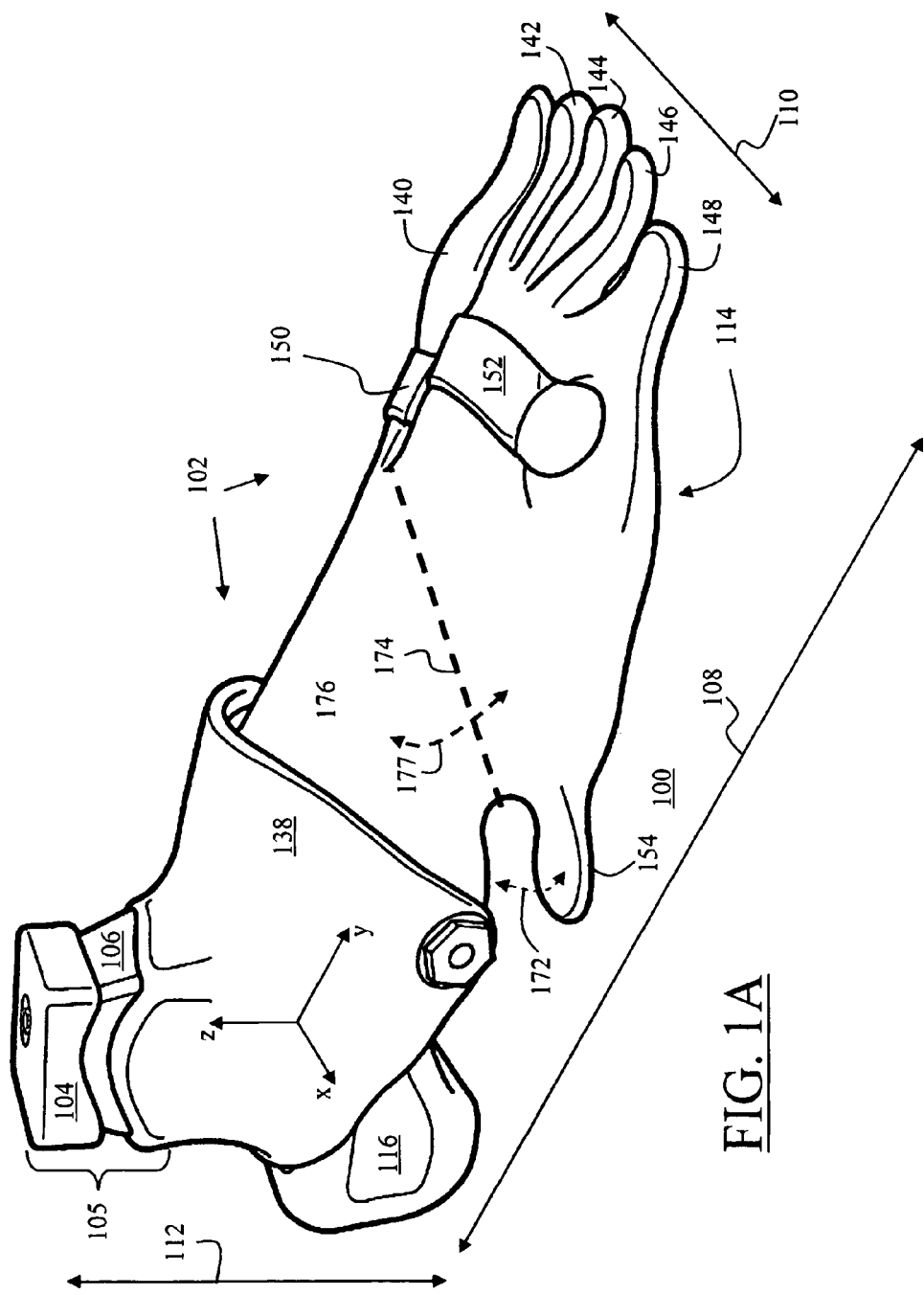
FIG. 1A is an exemplary perspective view of a prosthetic extremity that is comprised of a prosthetic foot assembly and prosthetic ankle assembly in accordance with the present invention.

FIG. 1A is an exemplary perspective view of a prosthetic extremity 100 that is comprised of a prosthetic foot assembly 102 and prosthetic ankle assembly 105 that closely resembles the anatomy of the human ankle and foot in terms of structure and operation, and closely mimics the natural motions of both the foot and the ankle.

The prosthetic foot 102 and ankle 105 of the present invention includes an ankle joint elastomer 106 that enables motion of the prosthetic foot assembly 102 around three perpendicular axes, as well as varying degrees of flexure. For purposes of discussion, the x, y, and z axes, about which the foot assembly 102 is designed to articulate (or rotate), are shown and have been assigned as follows. The x axis is transverse the longitudinal axis 108 of the foot assembly 102 (parallel with the transverse axis 110). In other words, the x axis is perpendicular to both the leg (not shown) and foot assembly 102, passing through the sides of the ankle assembly 105. The y axis is parallel the longitudinal axis 108 of the foot assembly 102. That is, the y-axis is perpendicular to the leg (not shown) and parallel to the foot assembly 102, and the z axis is parallel to the vertical axis 112 of the foot assembly 102, parallel to the leg (not shown).

Figure 1B:
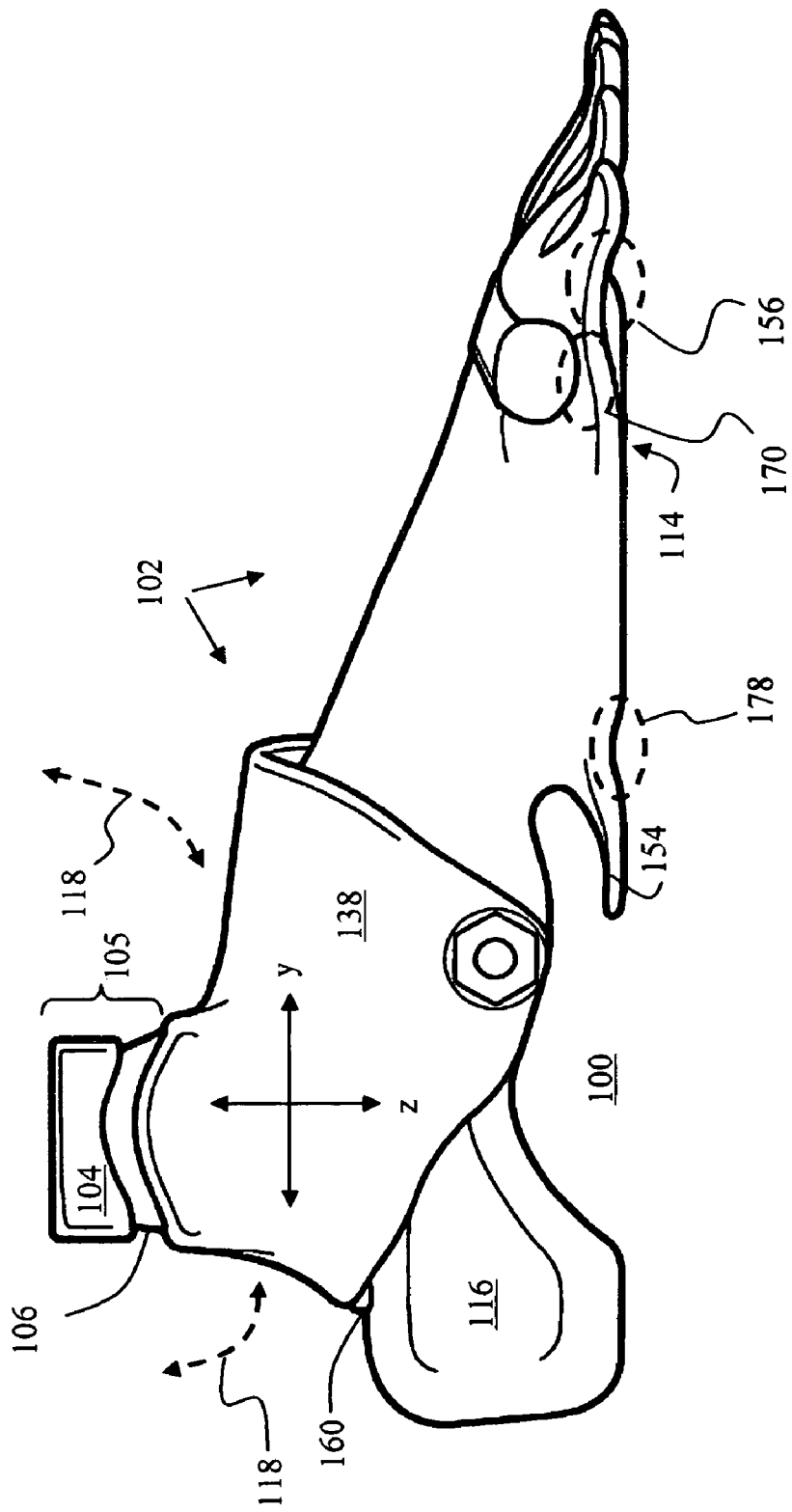
FIG. 1B is an exemplary first lateral view of the prosthetic extremity of FIG. 1A, showing the outer (or Fibular) side thereof.

The prosthetic extremity 100 of the present invention, including the prosthetic foot assembly 102 and prosthetic ankle assembly 105 is capable of a primary set of articulations, including dorsiflexion, planiflexion, inversion, eversion, and transverse rotation. That is, as best illustrated in FIG. 1B, the prosthetic foot assembly 102 and ankle assembly 105 are capable of primary articulations of dorsiflexion and planiflexion, which are up and down movements of the ball of the foot 114 with respect to the heel 116 that occur during a normal forward step (along the reciprocating path, illustrated by dashed arrows 118). Further, as best illustrated in FIGS. 1C and 1D, the prosthetic foot 102 and ankle 105 assemblies enable primary articulations of inversion and eversion, which are the twisting of the prosthetic foot assembly 102 around its longitudinal axis 108 (the y-axis), resulting in respective outward and inward tilting of the prosthetic ankle assembly 105 (along the reciprocating path, illustrated by the dashed arrows 120). Finally, as best illustrated in FIG. 1E, the prosthetic foot 102 and ankle 105 assemblies of the present invention enable primary articulation of transverse rotation, which occurs when the foot assembly 102 rotates with respect to the z axis (the vertical axis) parallel to the leg (not shown), for example during left and right turns of the body (along the reciprocating path, illustrated by the dashed arrows 130).

Figure 1E:
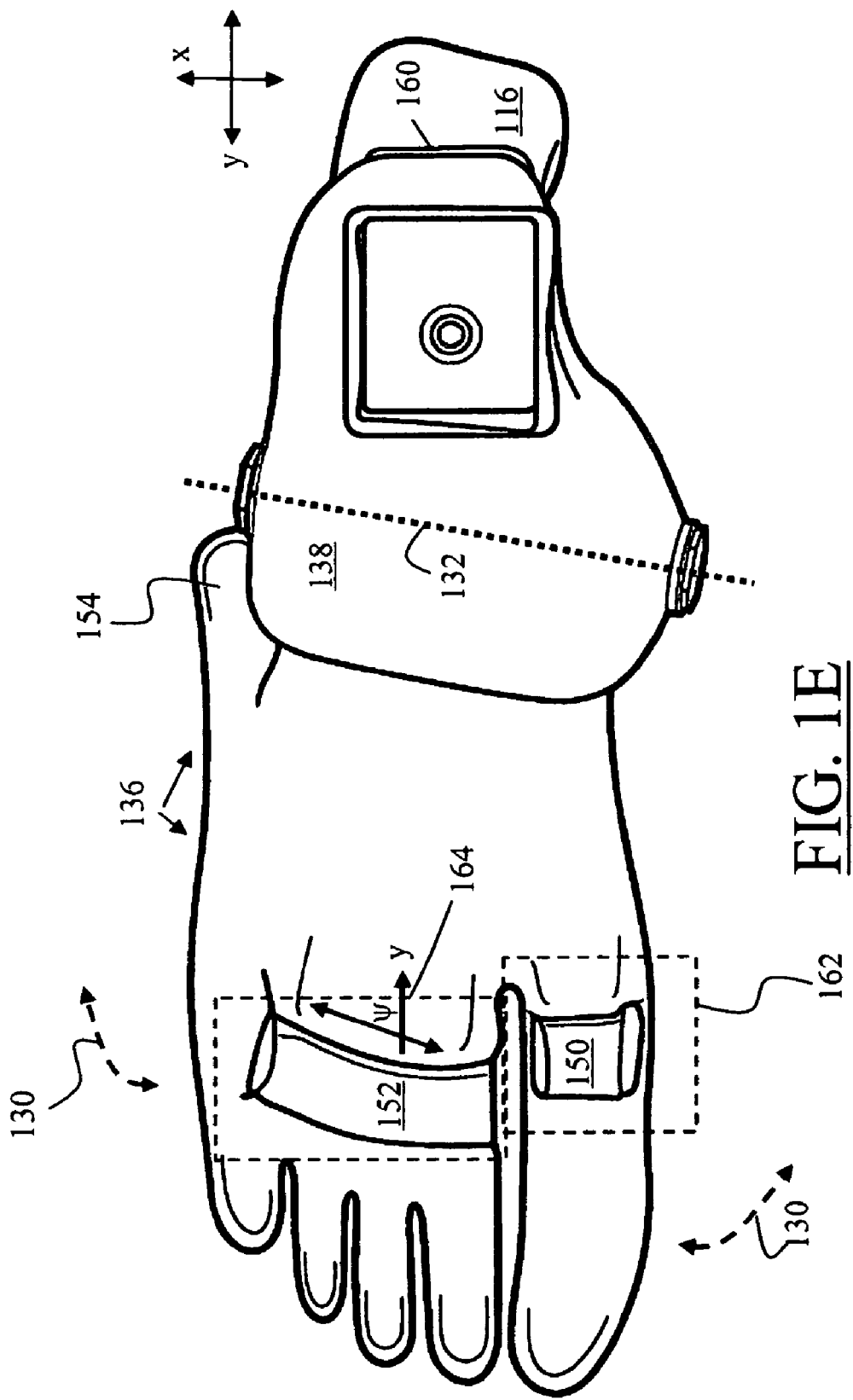
FIG. 1E is an exemplary plan top view of the prosthetic extremity of FIG. 1A.
Figure 1F:
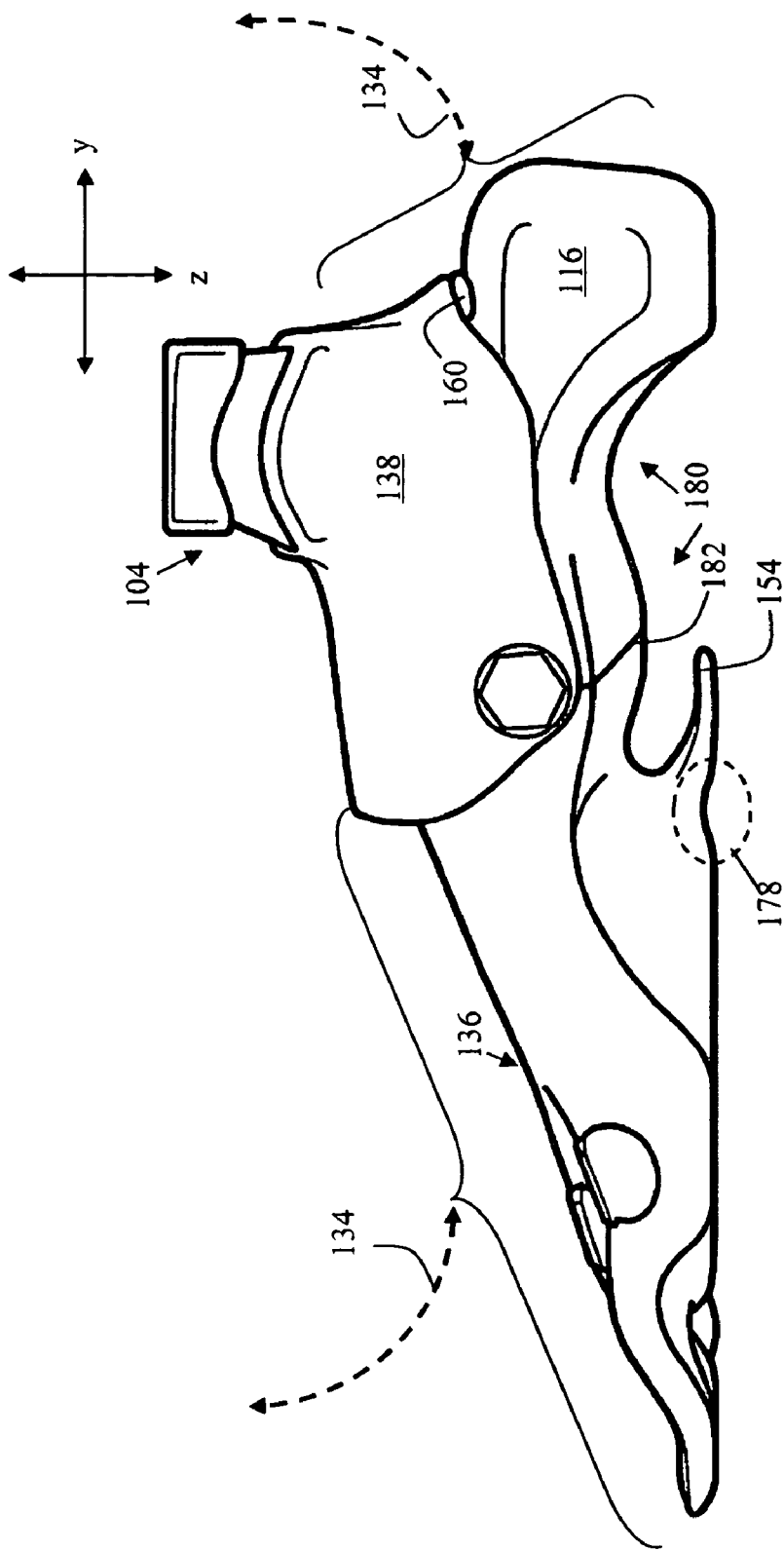
FIG. 1F is an exemplary perspective lateral view of the prosthetic extremity of FIG. 1A, showing the inner (or tibia) side thereof.

As best illustrated in FIGS. 1E and 1F, in addition to primary articulations, the prosthetic foot 102 and ankle 105 assemblies of the present invention provide a secondary articulation that is comprised of an arch flex motion 134 about an arch flex pivot axis 132, which enable a fore foot proximal end and a heel proximal end to travel in a reciprocal arc 134 defined by the arch flex pivot axis 132.

Further, the prosthetic extremity 100 of the present invention provides a set of tertiary articulations, resulting from the prosthetic extremity 100 from being able to absorb, store, and release energy so that the prosthesis returns itself to a relaxed, unflexed position when the moving force is removed (shown throughout the various figures). The primary, secondary, and tertiary articulations of the prosthetic extremity 100 closely provide the natural gait characteristics of a human foot and ankle. That is, the extremity 100 provides a stable support for the user throughout a reasonable range of activities and permits the user to walk with a normal stride. To achieve this normal stride, the prosthetic extremity 100 flexes during walking as the foot continually moves through the heel-strike, foot-flat, and toe-off cycle. It also, throughout this cycle, provides transverse stability particularly at toe-off, when the entire weight of the user is applied to the forward portion of the prosthetic extremity 100. That is, the extremity 100 closely duplicates the side to side stability at the toe section of the fore foot 136 where weight can be exerted on each side of the foot assembly 102. The ankle joint includes torsional flexibility transverse to the up and down motion of the ankle assembly 105, which pivotally lowers and raises the foot.

Referring back to FIGS. 1A to 1G, the prosthetic extremity 100 of the present invention is comprised of an ankle assembly 105 coupled with a foot assembly 102 by an arch suspension yoke 138, with the ankle assembly 105 enabling primary articulations of the foot assembly 102. The foot assembly 102 having a plantar surface and a dorsal surface includes a heel 116 coupled with a fore foot 136 by the arch suspension yoke 138, with the arch suspension yoke 138 enabling secondary articulations of the foot assembly 102.

Figure 2A:
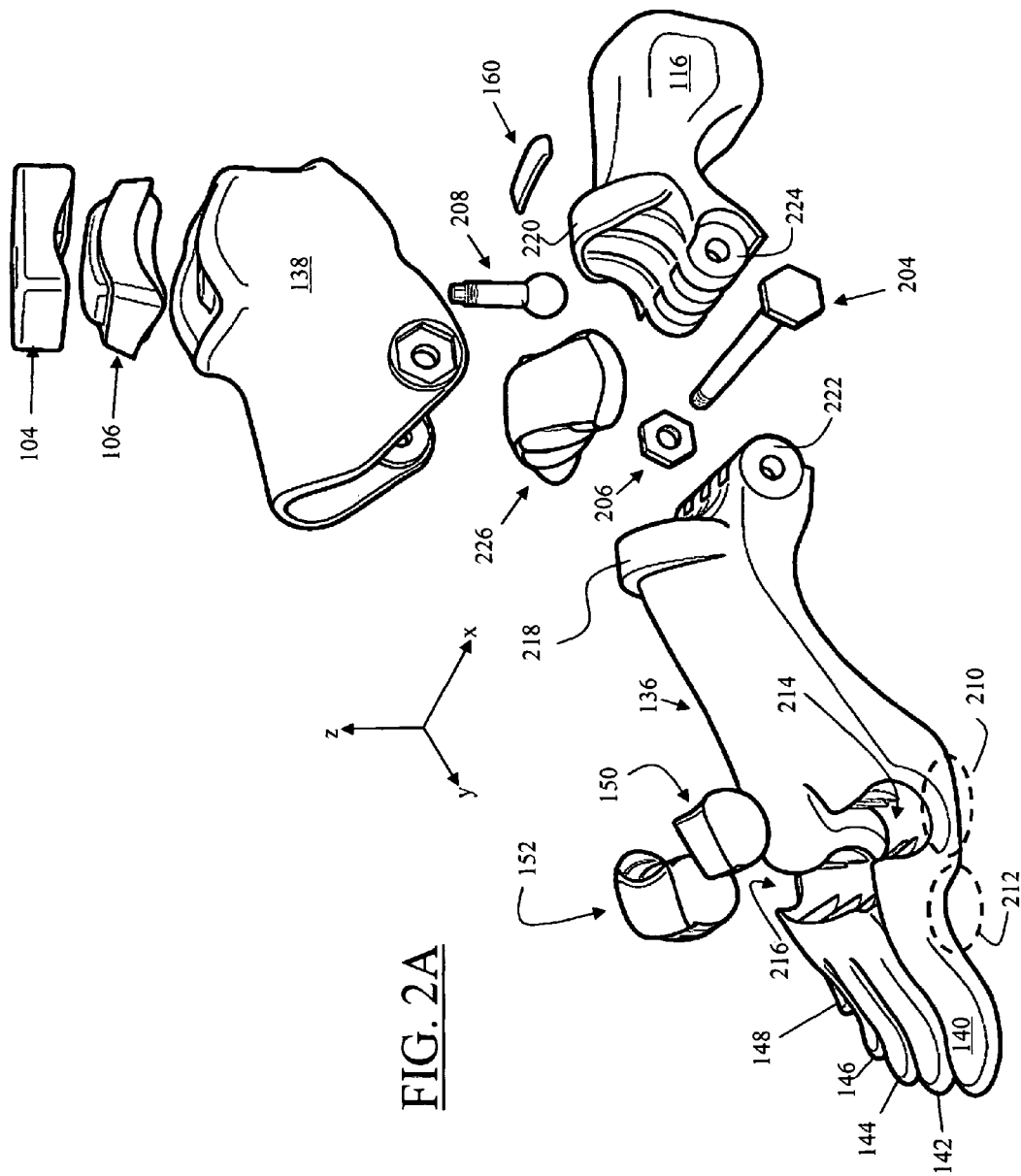
FIG. 2A is an exemplary exploded perspective view of the prosthetic extremity of FIG. 1A from the inner (or tibial) side thereof.
Figure 2B:
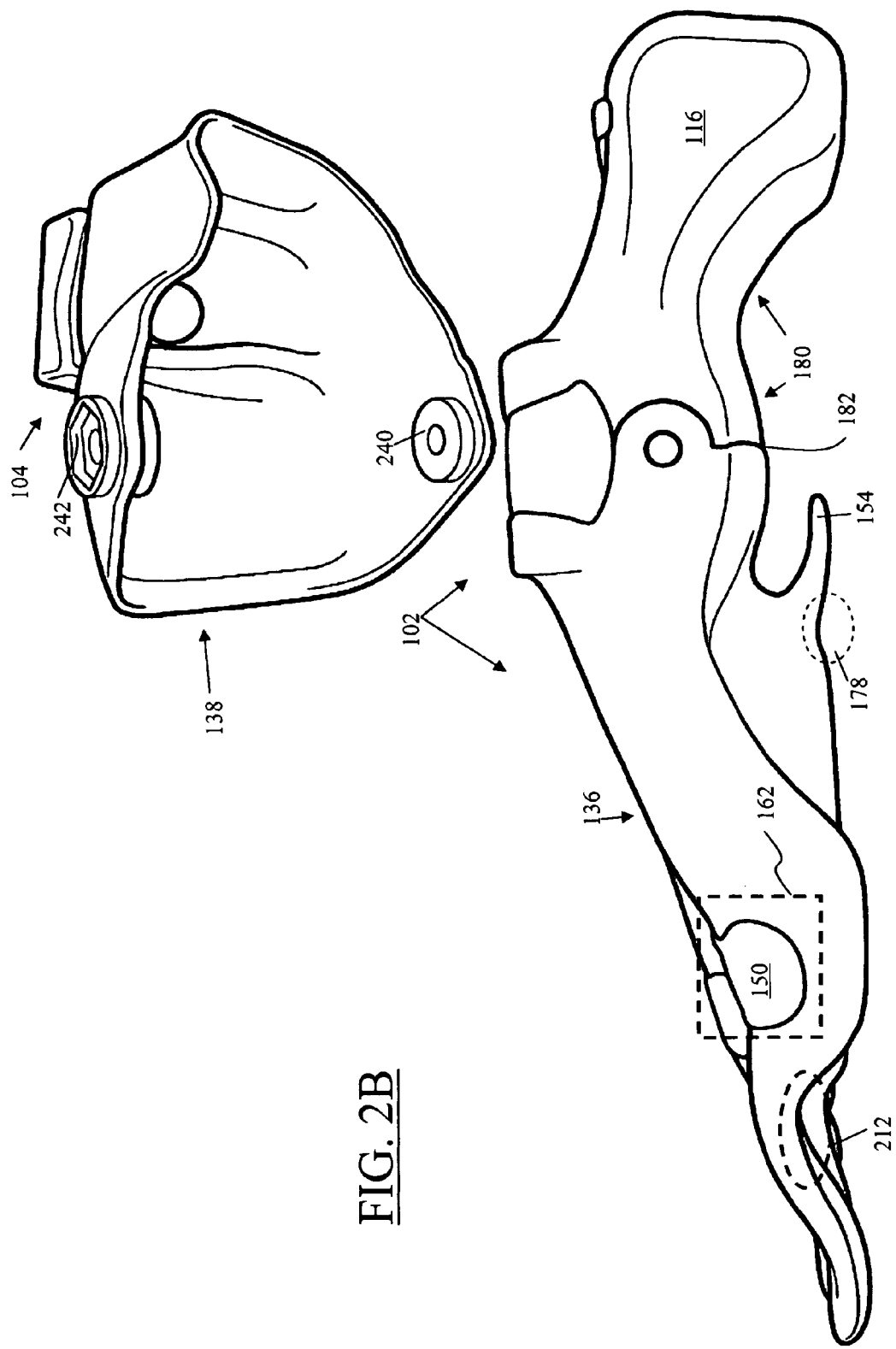
FIG. 2B is an exemplary lateral view of the prosthetic extremity of FIG. 1A with the arch suspension yoke partially removed, showing the foot assembly in accordance with the present invention.
Figure 2C:
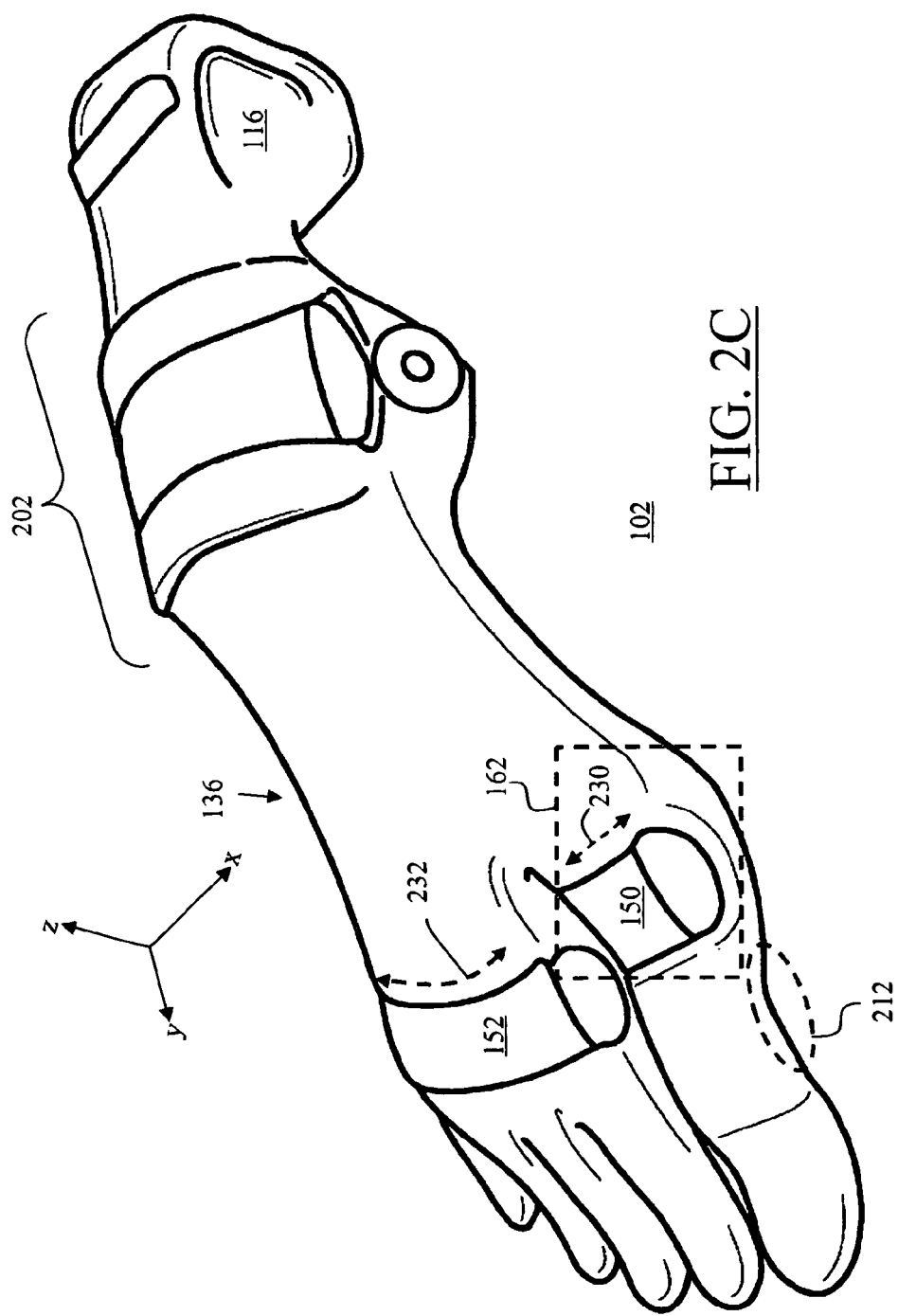
FIG. 2C is an exemplary perspective lateral view of the prosthetic extremity of FIG. 1A, showing only a perspective view of the foot assembly in accordance with the present invention.

FIG. 2A is an exemplary exploded perspective view (from inner or tibial side) of the prosthetic extremity of FIG. 1A, which will be referred to throughout the description. FIG. 2B is an exemplary lateral view of the prosthetic extremity of FIG. 1A with the prosthetic ankle assembly 105 and the arch suspension yoke 138 removed, showing the prosthetic foot assembly 102 in accordance with the present invention, and FIG. 2C is an exemplary lateral perspective view of the prosthetic foot assembly 102 in accordance with the present invention. As illustrated in FIGS. 2B and 2C, the foot assembly 102 is comprised of a fore foot 136 that is coupled with a heel 116 by a hinge biasing mechanism 202, which allows for secondary articulations 134 of the prosthetic extremity 100.

Figure 3A:
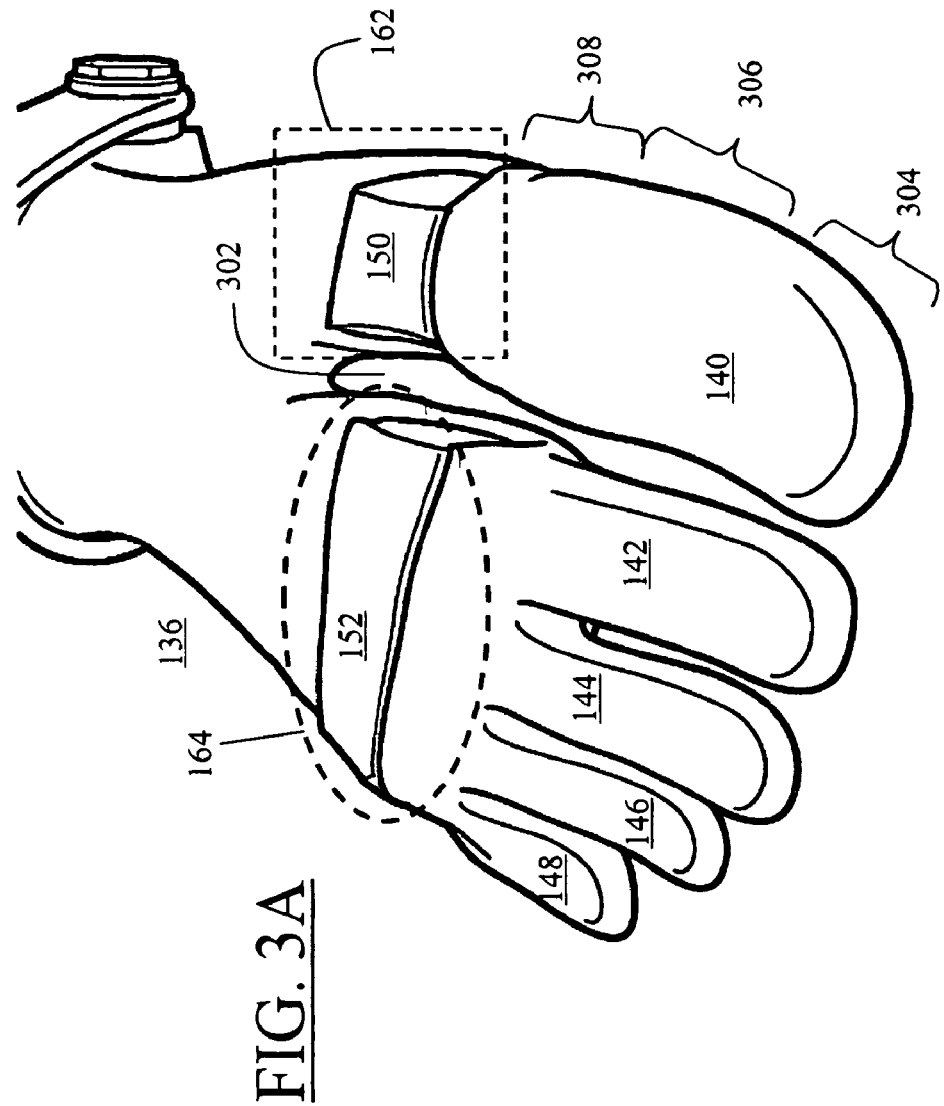
FIG. 3A is an exemplary perspective frontal view of the fore foot of the prosthetic extremity of FIG. 1A.
Figure 3B:
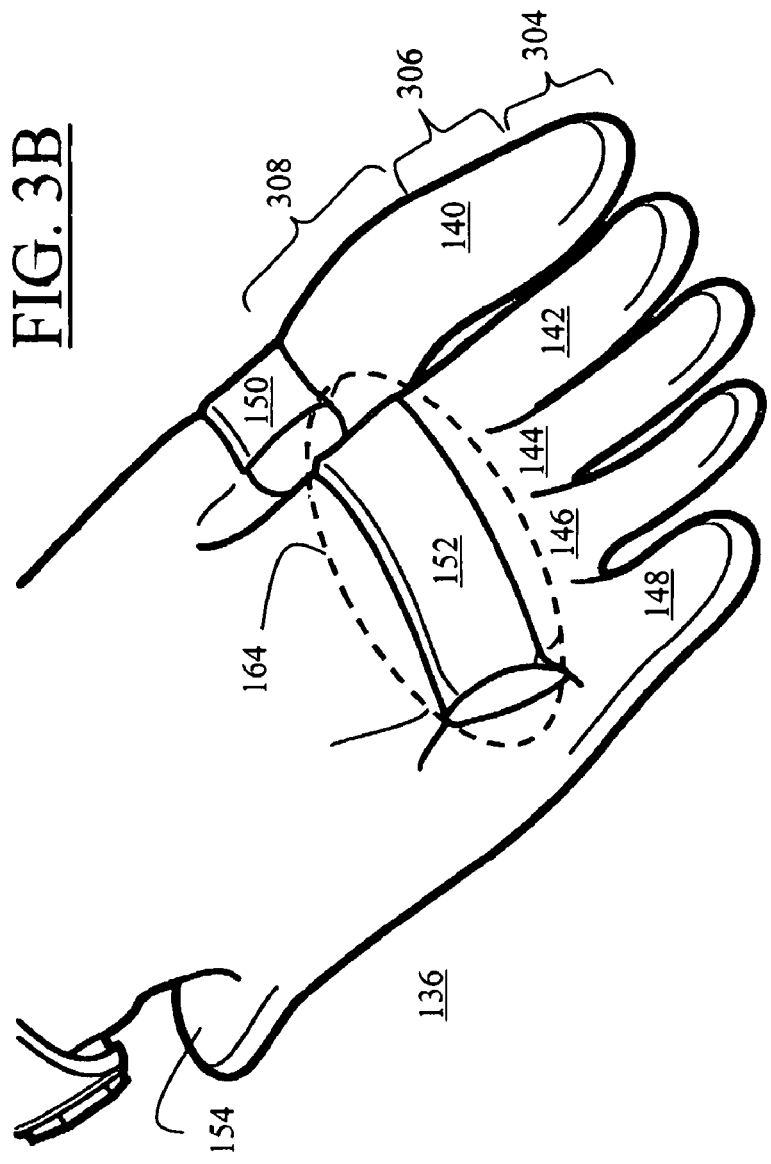
FIG. 3B is an exemplary perspective side-frontal view of the fore foot of the prosthetic extremity of FIG. 1A.
Figure 3C:
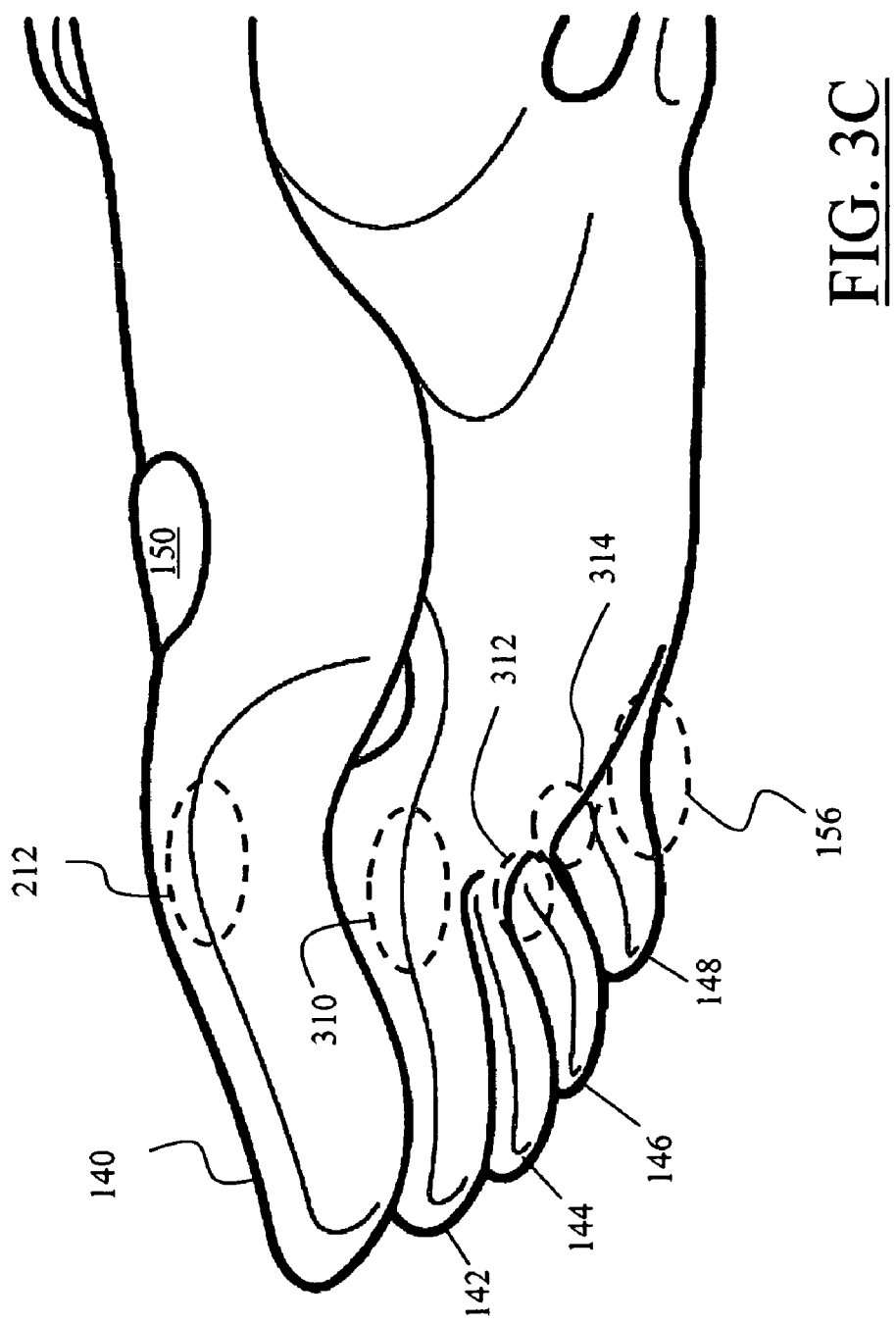
FIG. 3C is an exemplary bottom-side perspective view of the fore foot of the prosthetic extremity of FIG. 1A.
Figure 3D:
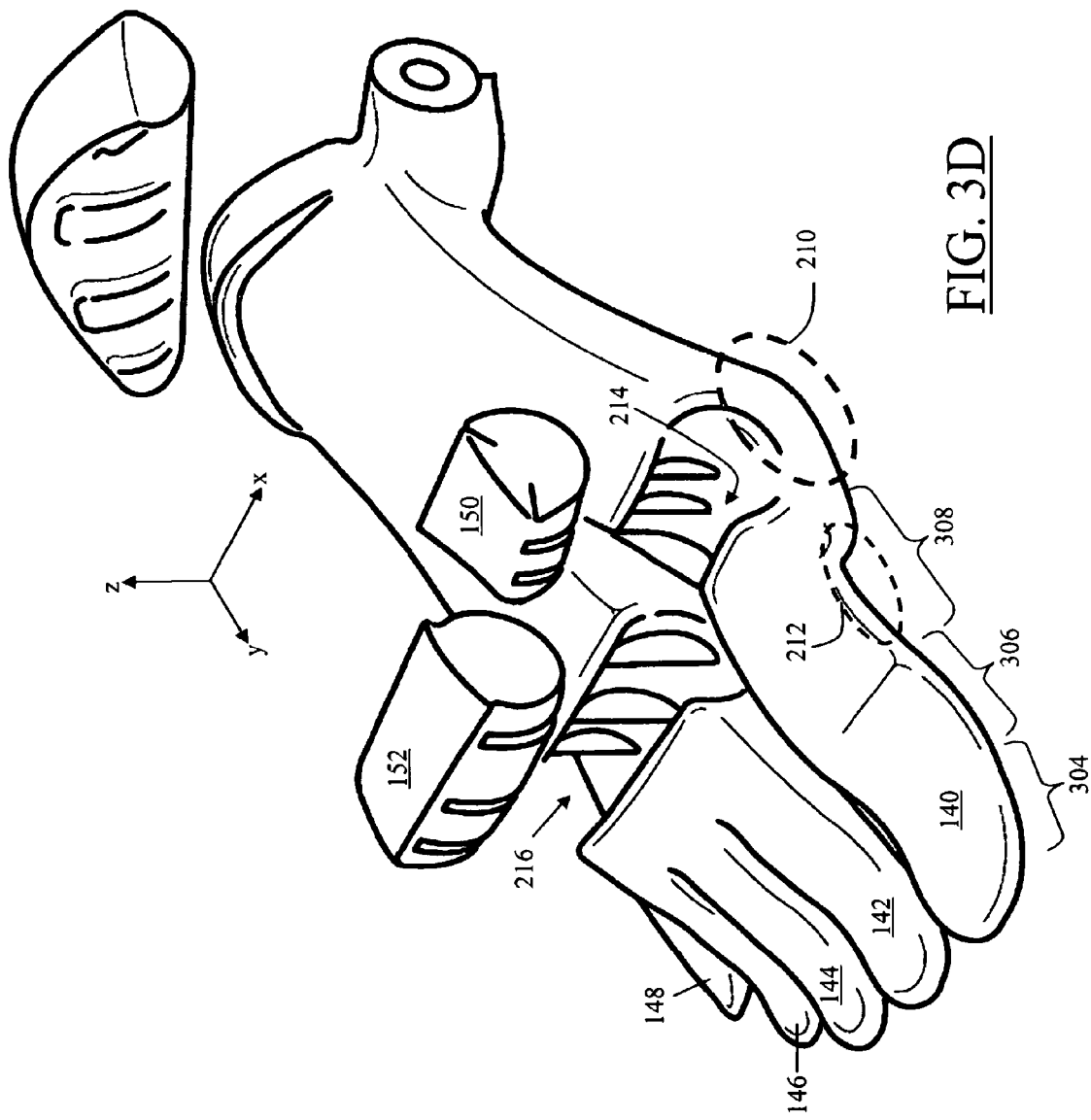
FIG. 3D is an exemplary exploded perspective inner side (tibia) frontal view of the fore foot of the prosthetic extremity of FIG. 1A.
Figure 3E:
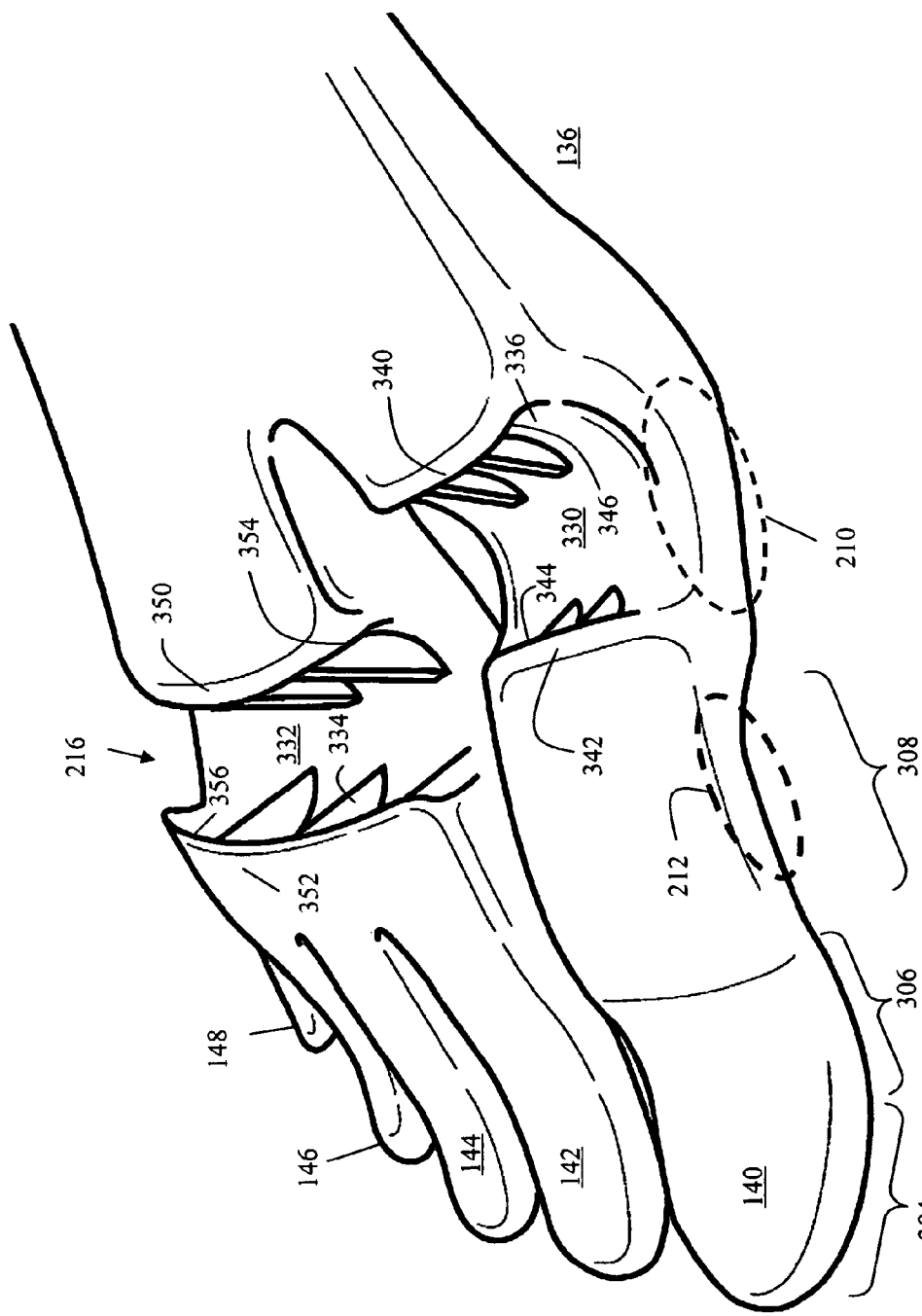
FIG. 3E is an exemplary perspective inner side (tibia) frontal view of the fore foot of the prosthetic extremity of FIG. 1A, without the elastomer springs.
Figure 3F:
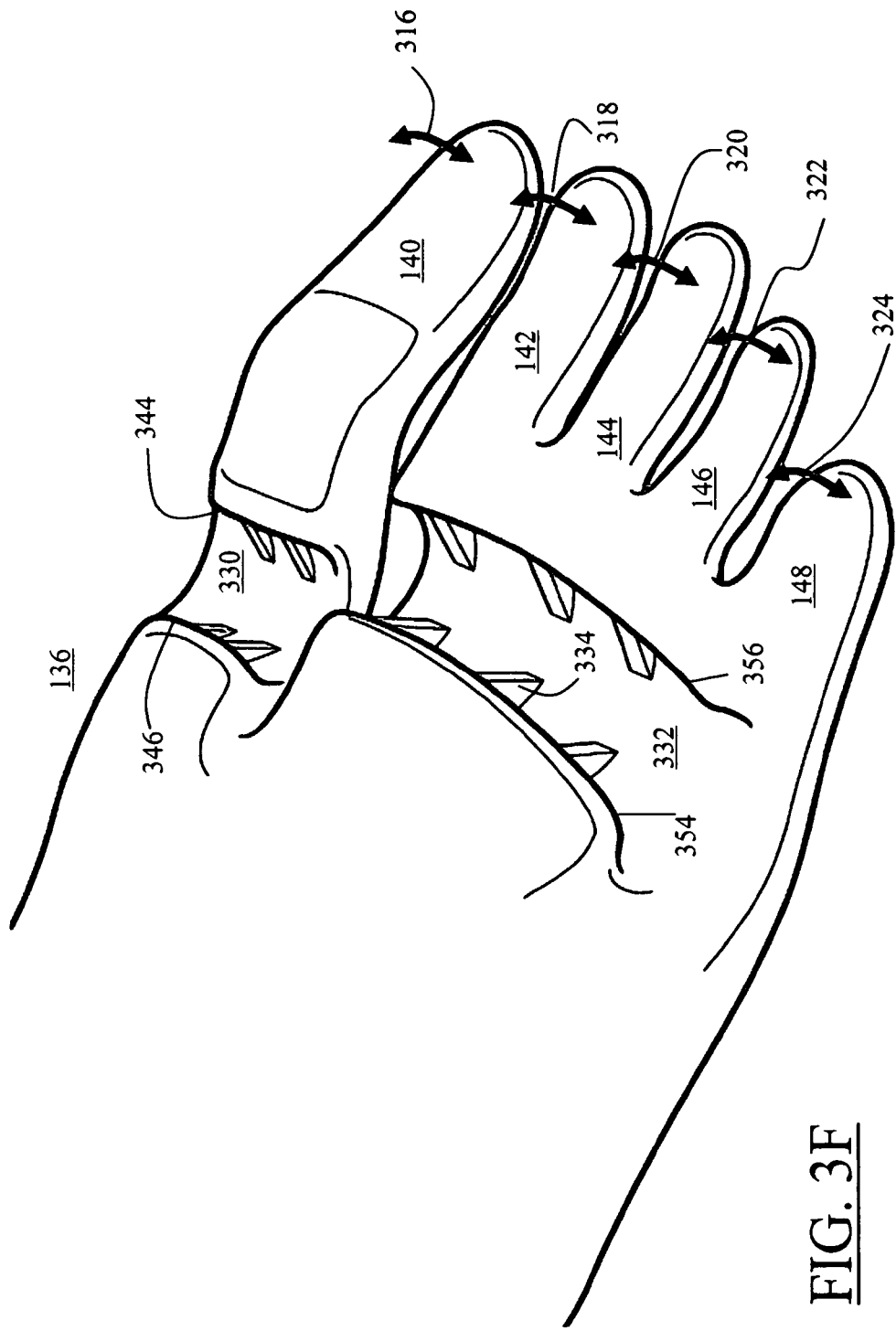
FIG. 3F is an exemplary perspective outer (Fibula) frontal view of the fore foot of the prosthetic extremity of FIG. 1A without the elastomer springs.

As best illustrated in FIGS. 3A to 3F, the fore foot 136 of the prosthetic foot assembly 102 includes a primary section configured as prosthetic phalanges. The primary section of the fore foot includes individually separate first toe 140, a second toe 142, a third toe 144, a fourth toe 146, and a fifth toe 148, with each toe comprising a single piece unit having dorsal and plantar surfaces. Both the dorsal and planter surfaces of all toes have substantially flat toe distal end 304 continued obliquely to a raised toe median section 306 that ends at a toe proximal end 308. As best illustrated in FIGS. 3C and 3F, the toe median section 306 forms a toe leaf spring 212, 310, 312, 314, and 156 for each respective toe 140, 142, 144, 146, and 148 enabling individual, respective tertiary articulations in the reciprocating paths 316, 318, 320, 322, and 324 of the respective first toe 144, the second toe 142, the third toe 144, the fourth toe 146, and the fifth toe 148. The primary section of the fore foot 136 further includes an abbreviated interosseous space 302 (FIG. 3A) between the first toe 140 and the second toe 142, enabling greater range of movement for the first toe 140 to facilitate counter balancing, push-off of the foot from the ground, and increased dexterity.

As further illustrated in FIGS. 3A to 3F, the fore foot 136 of the prosthetic foot assembly 102 also includes a secondary section configured as metatarsal joints in the form of a first biasing mechanism 162 (FIG. 1E) with a first axial length 230 (FIG. 2C) and a second biasing mechanism 164 with a second axial length 232 that is longer than the first axial length 230. As illustrated, the first axial length 230 is oriented substantially transverse the longitudinal axis 108 (y-axis) of the foot assembly 202, and the second axial length 232 is oriented at an angle ψ (FIG. 1E) to the longitudinal axis 108 of the foot assembly 202.

The respective first and the second biasing mechanisms 162 and 164 are substantially cylindrical, with both the first and second biasing mechanisms 162 and 164 having a center line axis that is slightly bent (best viewed in FIG. 1E). Further, the first biasing mechanism 162 is positioned slightly posterior the second biasing mechanism 164. As further illustrated, the first biasing mechanism 162 and the second biasing mechanism 164 are comprised of a substantially "C" shaped toe spring cavity 214 and 216 for housing respective elastomer springs 150 and 152. The substantially "C" shaped toe spring cavity 214 and 216 include a joint leaf springs 170 (FIG. 1B) and 210 (FIG. 2A) extending longitudinally along an axial length of a bottom surface 330 and 332 of the respective toe spring cavity 214 and 216.

As best illustrated in FIGS. 3E and 3F, the toe spring cavity 214 and 216 of the respective first and second biasing mechanisms 162 and 164 include elongated canals with a plurality of flanges 334. The flanges 334 are aligned laterally along an axial length of the toe spring cavity 214 and 216, forming an alternating protuberance 334 and depression 336 within the toe spring cavity 214 and 216. The dorsal, inner bottom surface 330 and 332 of the toe spring cavity 214 and 216 is smooth and concaved, with the plantar, outer surface substantially flat, forming the joint leaf spring 170 and 210.

Figure 4B:
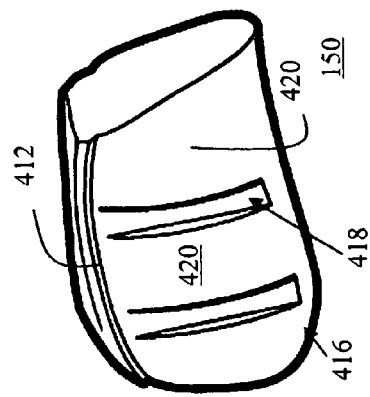
FIGS. 4A to 4C are exemplary views of a first elastomer spring of the fore foot of the prosthetic extremity of FIG. 1A.
Figure 4C:
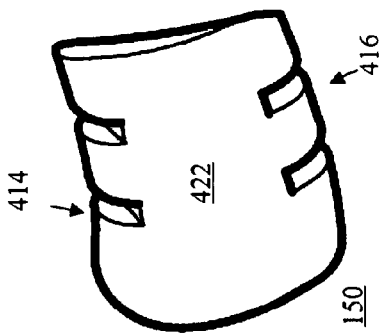
Figure 4A:
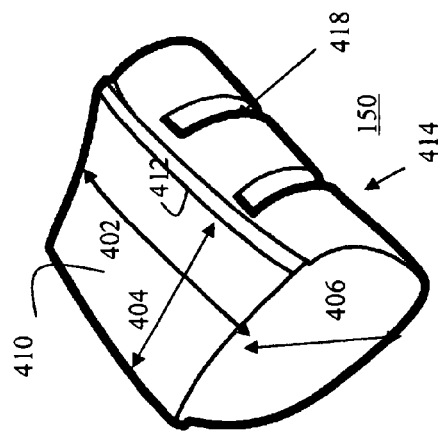

As best illustrated in FIGS. 3D, and 4A to 4F, and in particular FIGS. 4A to 4C, the elastomer spring 150 of the first biasing mechanism 162 is comprised of an elastomer having an axial length 402, a width 404, and a thickness 406. The elastomer 150 includes a top surface 410 that includes slightly convex section that is extended longitudinally, along the axial length 402 of the elastomer spring 150. The convex shape effects the manner by which the elastomer spring 150 counters applied forces. The slightly convex section top surface 410 includes lateral edge depressions 412 extending longitudinally, along the axial length 402 of both lateral sides 414 and 416 of the elastomer spring 150. The elastomer spring 150 further includes the two lateral side surfaces 414 and 416 that extend longitudinally along the axial length 402 of the spring 150. The lateral side surfaces 414 and 416 include a plurality of notches 418 that are formed into the lateral side surfaces 414 and 416 of the elastomer spring 150. The notches 418 are aligned laterally along the axial length 402 of the spring 150, forming an alternating notch 418 and protuberance 420. Each notch of the plurality of notches 418 is comprised of a substantially flat base, from which, perpendicular protrusions are extended to form two side walls of each notch 418. The elastomer spring 150 further includes a smooth, bottom surface 422. As best illustrated in FIG. 3D, the spring 150 with its plurality of notches 418 is positioned within the toe spring cavity 214 such that each notch 418 is biased against a corresponding protrusion 334 on the toe spring cavity 214. The spring 150 contacting the toe spring cavity 214 and biasing the toe spring cavity 214 so that the toe spring cavity 214 counter-rotates about the center line axis of the first biasing mechanisms 162. The toe spring cavity 214 also includes a top 340 and 342 having a length that extends longitudinally along an axial length 230 of the toe spring cavity 214 and a width forming a lip 344 and 346. The two lateral edge depressions 412 securely abut the lip 344 and 346 of the toe spring cavity 214.

The elastomer spring 150 has a first surface contact area with a first mass having a durometer that provides a first resistance and a first rate of resistance responsive to application of forces. The spring 150 also has a second surface contact area with a second mass having the same durometer that provides a second resistance and a second rate of resistance responsive to the forces. The first resistance and the first rate of resistance are different from the second resistance and second rate of resistance, a combination of which provides a rate of resistance that commensurately varies and is correspondingly responsive in relation to varying forces. Another aspect of the present invention provides a method for varying a resistive response and resistive rate of response of spring 150, comprising increasing a contact surface area and lowering a mass of the spring by providing two mass regions and two surface contact areas, including a first surface contact area with a first mass having a durometer that provides a first resistance and a first rate of resistance responsive to application of forces. Also provided, is a second surface contact area with a second mass having the same durometer that provides a second resistance and a second rate of resistance responsive to the forces. The first resistance and the first rate of resistance different from the second resistance and second rate of resistance, a combination of which provides a rate of resistance that commensurately varies and is correspondingly responsive in relation to varying forces.

All elastomer springs used throughout the present application are fully described in U.S. Utility patent application Ser. No. 11/985,473, filed Nov. 15, 2007, now pending, the entire disclosure of which is expressly incorporated by reference.

Figure 4E:
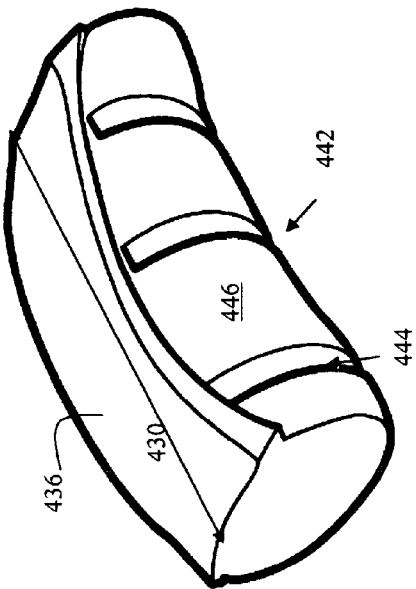
FIGS. 4D to 4F are exemplary views of a second elastomer spring of the fore foot of the prosthetic extremity of FIG. 1A.
Figure 4F:
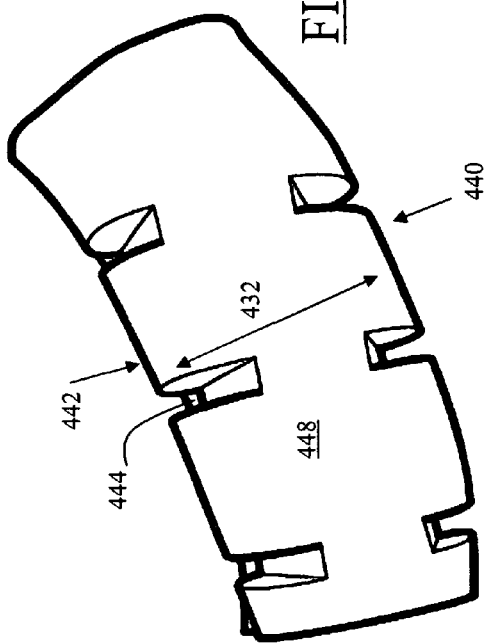
Figure 4D:
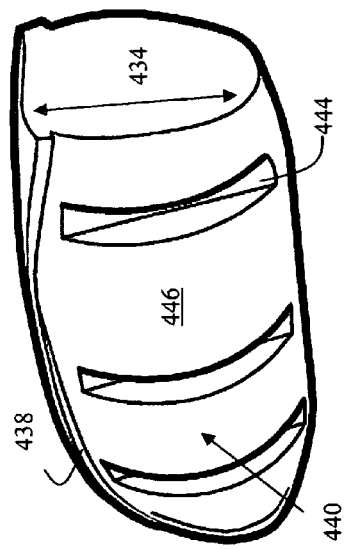

As best illustrated in FIGS. 3D, and 4A to 4F, and in particular FIGS. 4D to 4F, the second elastomer spring 152 of the second biasing mechanism 164 is comprised of an elastomer having an axial length 430, a width 432, and a thickness 434. The elastomer 152 includes a top surface 436 that includes slightly convex section that is extended longitudinally, along the axial length 430 of the elastomer spring 152. The convex shape effects the manner by which the elastomer spring 150 counters applied forces. The slightly convex section top surface 436 includes lateral edge depressions 438 extending longitudinally (on both sides of the spring 152), along the axial length 430 of the spring 152. The elastomer spring 152 further includes two lateral side surfaces 440 and 442, and extending longitudinally along the axial length 430 of the spring 152. The lateral side surfaces 440 and 442 include a plurality of notches 444 that are formed into the lateral side surfaces 440 and 442 of the spring 152. The notches 444 are aligned laterally along the axial length 430 of the spring 152, forming an alternating notch 444 and protuberance 446. Each notch of the plurality of notches 444 is comprised of a substantially flat base, with two perpendicular side walls. The spring 152 further includes a smooth, bottom surface 448. As best illustrated in FIG. 3D, the spring 152 with its plurality of notches 444 is positioned within the toe spring cavity 216 such that each notch 444 is biased against a corresponding protrusion 334 on the toe spring cavity 216. The elastomer spring 152 contacting the toe spring cavity 216 and biasing the toe spring cavity 216 so that the toe spring cavity 216 counter-rotates about the center line axis of the second biasing mechanisms 164. The toe spring cavity 216 also includes a top 350 and 352 having a length that extends longitudinally along an axial length 232 of the toe spring cavity 216 and a width forming a lip 354 and 356. The two lateral edge depressions 438 securely abut the lip 354 and 356 of the toe spring cavity 216. It should be noted that the notches 418 on the first elastomer spring 150 are narrower than those (notches 444) found on the second elastomer spring 152. The wider notch 444 provides a greater counter-resistance to applied forces as compared to the narrower notches 418 of the spring 150. This is to provide a greater control and direction in terms of resistance for the push-off of the foot from the ground.

As further illustrated in FIG. 1A, the fore foot 136 of the prosthetic foot assembly 102 also includes a tertiary section configured as prosthetic metatarsals 176, including an oblique, dorsal surface forming an asymmetrical convex configuration extending transversely, oriented parallel the width of the foot assembly 102 from an inner side of foot assembly 102 to an outer side of the foot assembly 102. Further included is a balancing protuberance 154 in the outer side of the foot assembly 102 extending parallel along longitudinal axis of the foot assembly 102, which is proximal the arch pivot axis 132, and includes a balancing leaf spring 178 (FIG. 1B). Also included is a fore foot main arch 180 (FIG. 1F) at the inner side of the foot assembly 102. As best illustrated in FIG. 1A, tertiary articulations are achieved in the reciprocating paths indicated by the arrows 172 and 177 for the respective balancing protuberance 154 and the prosthetic metatarsals 176. The tertiary articulation 177 is achieved by bending of the lower section of the metatarsal 176 about the axial line 174. The tertiary articulation 177 provides for diagonal (laterally) flexibility for greater dexterity. In other words, it enables the extremity 100 to closely duplicate the side to side stability at the toe section of the fore foot 136 where weight can be exerted on each side of the foot assembly 102.

Figure 1G:
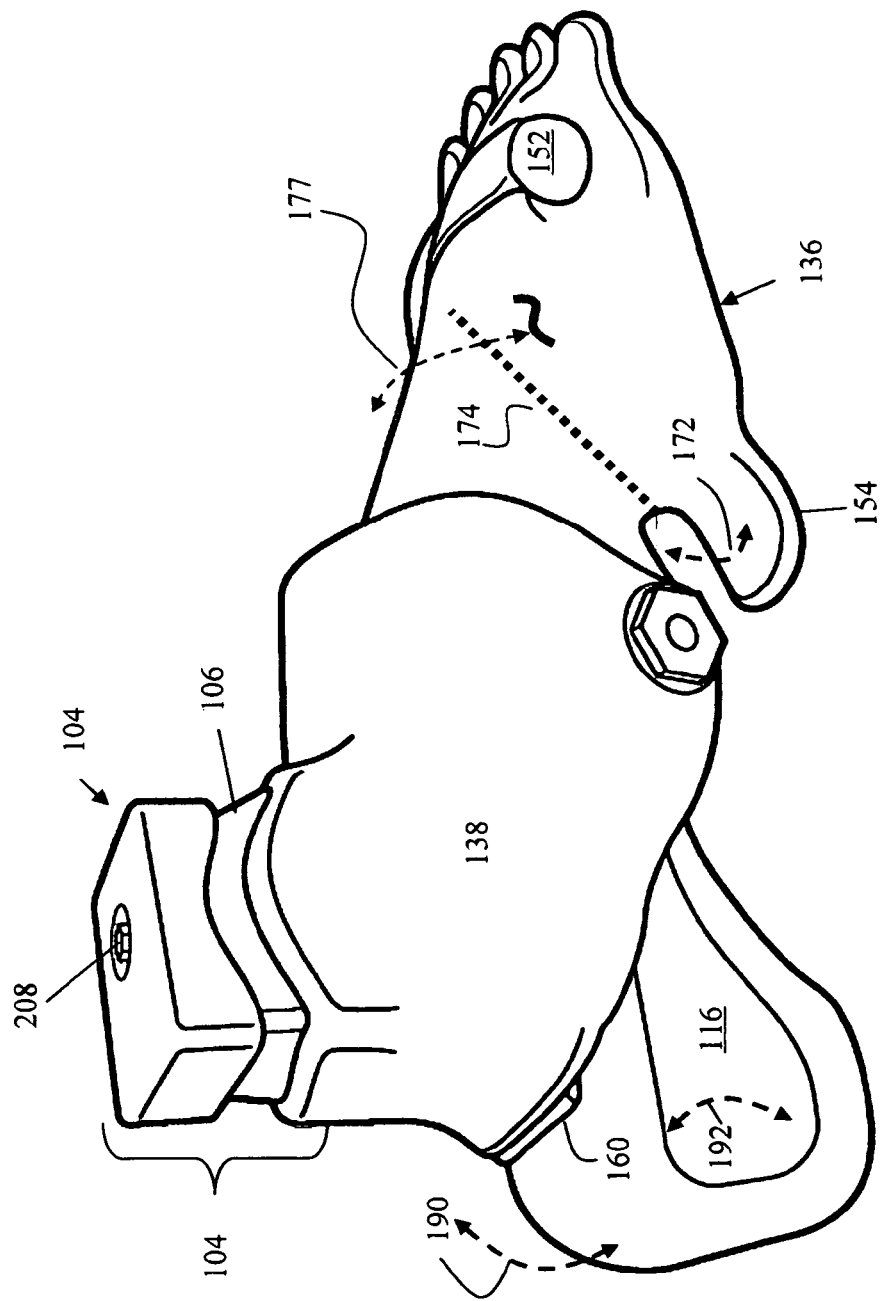
FIG. 1G is an exemplary perspective posterior view of the prosthetic extremity of FIG. 1A, showing the outer (or Fibular) side thereof.

As further illustrated in FIG. 1G, tertiary articulations are also achieved in the reciprocating paths indicated by the arrows 190 and 192 for heel 116. The tertiary articulation 190 and 192 is achieved by inward and outward rolls (inversion/eversions) 190 and up and down (dorsiflexion/planiflexion) articulations of the heel 116 during normal gaiting for greater dexterity. As with other tertiary articulations, movements 190 and 192 enable the extremity 100 to closely duplicate the side to side and up and down stability at the posterior section of the foot assembly 102.

As further illustrated in FIGS. 1A and 2A, the fore foot 136 of the prosthetic foot assembly 102 also includes an asymmetrical quaternary section for coupling the fore foot 136 with the heel 116, arch suspension yoke 138, and the ankle assembly 105. The quaternary section (best illustrated in FIGS. 5A to 5D) includes a first section 502 of the hinge biasing mechanism 202 having a longitudinal axis 504 oriented at an angle $\theta$ to the longitudinal axis 108 of the foot assembly 102, and tilted down at an angle $\psi$ from an inner fore foot to the outer fore foot. The first section 502 of the hinge biasing mechanism 202 further includes fore foot hinge barrels 222, which are oriented transverse the longitudinal axis 108 of the foot assembly 102. The fore foot hinge barrels 222 are comprised of integrally circular, hollow sections forming a set of fore foot pivot knuckles of a main hinge. The set of fore foot pivot knuckles 222 are inserted within spaces 606 (FIG. 6A) of the second section 530 of the hinge biasing mechanism 202 and interlocked with a set of heel pivot knuckles 224, with the integrally circular, hollow sections of the set of fore foot pivot knuckles and the heel pivot knuckles aligned, through which a main pin 204 is inserted coupling the set of fore foot pivot knuckles 222 and the heel pivot knuckles 224, forming the main hinge.

The first section 502 of the hinge biasing mechanism 202 further includes a first section wall 514, having a plurality of vertically oriented flanges 516 with smooth, rounded surfaces that are aligned laterally along the first section wall 514. Further, the first section 502 of the hinge biasing mechanism 202 also includes a first section top 218 having a length that extends longitudinally along an axial length 504 of the hinge biasing mechanism 202 and has a width forming a first lip 510. A first top surface 710 (FIG. 7A) of a third spring 226 includes a first lateral edge depression 712 that securely abuts the first lip 510 of the first section 502 of the hinge biasing mechanism 202. The other, opposite side of the first top section is a fore foot stop 508, which when contacted with the anterior inner surface 914 of the arch suspension yoke 138, prevents (or limits) further planiflexion of the fore foot 136, including the secondary articulations between the fore foot 136 and the heel 116. The first section 502 of the hinge biasing mechanism 202 further includes a lower end stop 520, which prevents further secondary articulations between heel and the fore foot 136. The stop 520 is further used to preload the third elastomer spring 226.

As best illustrated in FIGS. 6A to 6D, the prosthetic foot assembly 102 of the extremity 100 of the present invention is further comprised of a heel 116, which includes of a posterior heel section with part of the dorsal surface covered with a heel damper mechanism 160 (comprised of an elastomer), a heel arch 602, and a second section 530 of the hinge biasing mechanism 202. The second section 530 of hinge biasing mechanism 202 has a longitudinal axis 608 oriented at an angle $\theta$ to the longitudinal axis 108 of the foot assembly 102, and tilted down at an angle $\phi$ from an inner fore foot to an outer fore foot. The second section 530 of hinge biasing mechanism 202 includes heel hinge barrels 224, oriented transverse the longitudinal axis 108 of the foot assembly 102. The heel hinge barrels 224 are comprised of integrally circular, hollow sections forming a set of heel pivot knuckles, with spaces 606 in between, forming the main hinge. The set of heel pivot knuckles are inserted within spaces 522 (FIG. 5D) of the second section of the hinge biasing mechanism 202 and interlocked with the set of fore foot pivot knuckles 222, with the integrally circular, hollow sections of the set of fore foot pivot knuckles 522 and the heel pivot knuckles 524 aligned, through which the main pin 204 (FIG. 2A) is inserted coupling the set of fore foot pivot knuckles 522 and the heel pivot knuckles 524, forming the main hinge.

The second section 530 of the hinge biasing mechanism 202 further includes a second section wall 610, having a plurality of vertically oriented flanges 612 with smooth, rounded surfaces that are aligned laterally along the second section wall 610. The second section 530 of the hinge biasing mechanism 202 also includes a second section top 220 having a length that extends longitudinally along an axial length 608 of the hinge biasing mechanism 202 having a width that forms a second lip 614. The first top surface 710 of a third spring 226 includes a first lateral edge depression 712 that securely abuts the second lip 614 of the first section 530 of the hinge biasing mechanism 202. The other, opposite side of the second top section is a heel stop 620, which when contacted with the posterior inner surface of the arch suspension yoke 138, prevents further planiflexion of the heel 116, including the secondary articulations between the fore foot 136 and the heel 116. The first section 530 of the hinge biasing mechanism 202 further includes a second lower end stop 622, which prevents further secondary articulations between heel 116 and the fore foot 136. The stop 622 is further used to preload the third elastomer spring 226. As best illustrated in FIGS. 6E to 6G, the heel damper mechanism 160 is comprised of a substantially asymmetrical rectangular configuration with a bottom surface 602 and curved ends 604 that fits on the top surface of the posterior of the heel 116.

Figure 5A:
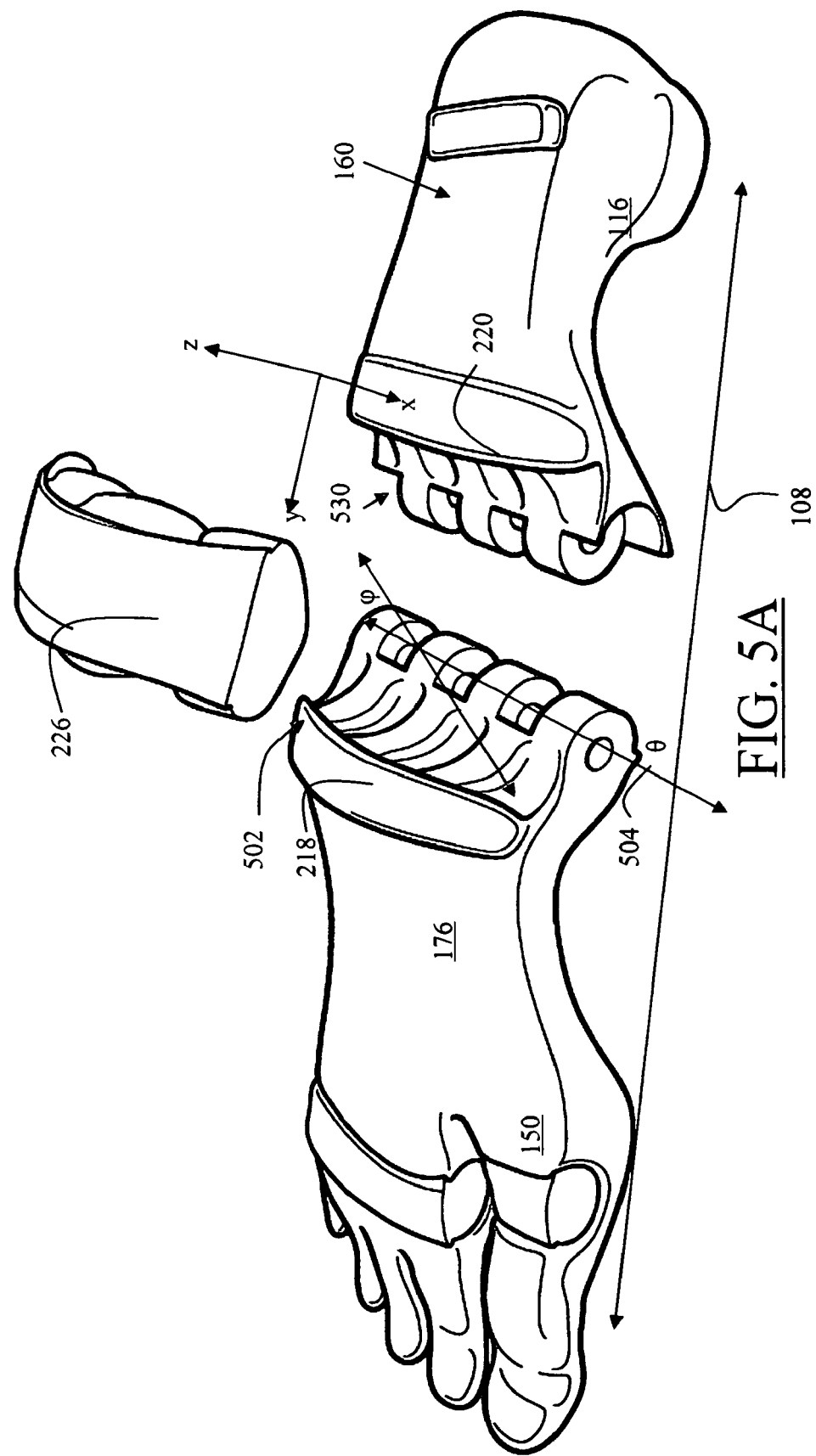
FIGS. 5A to 5C are exemplary exploded lateral perspective views of the prosthetic extremity of FIG. 1A, showing only a perspective view of the foot assembly in accordance with the present invention.
Figure 5B:
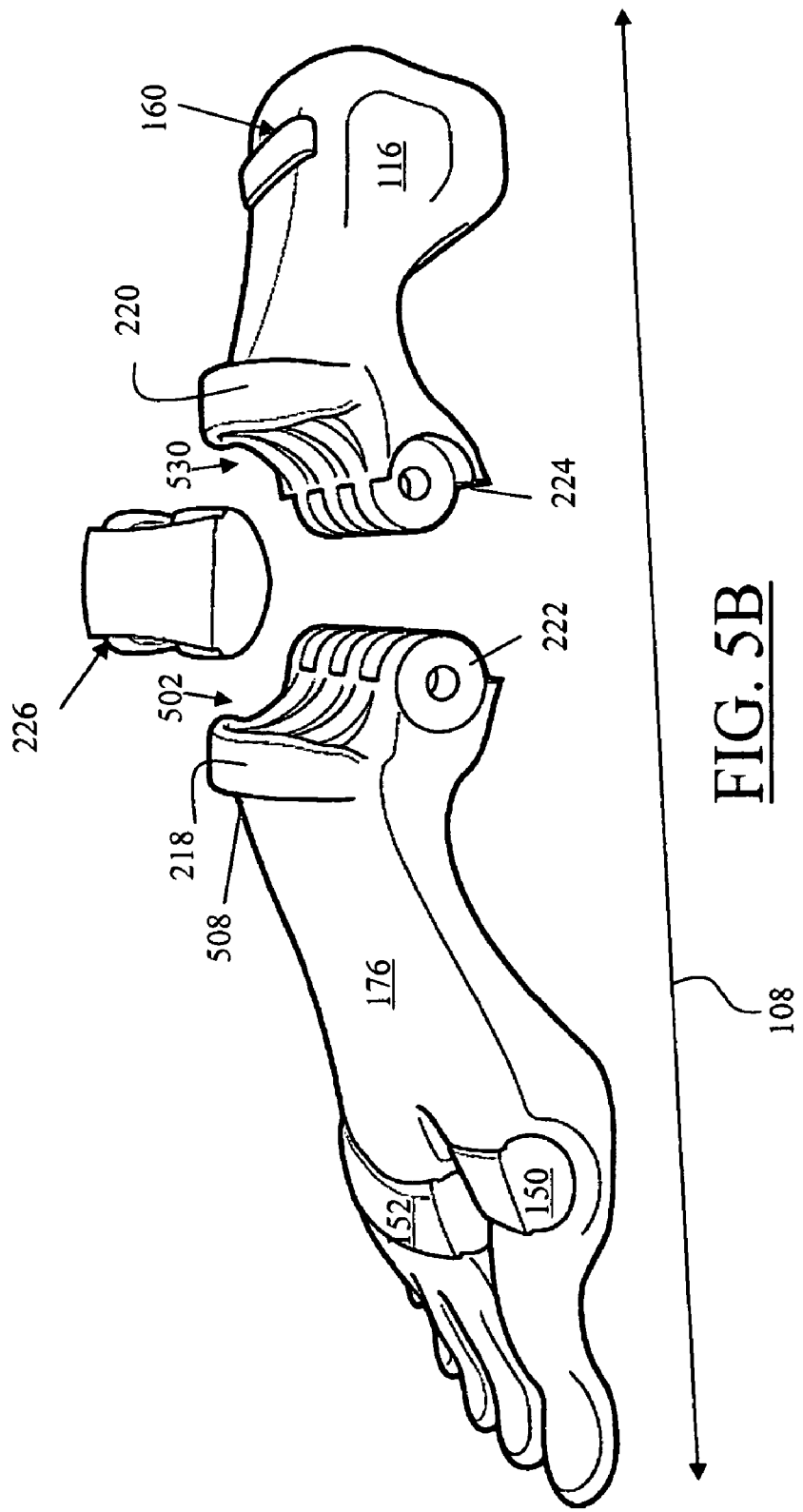
Figure 5C:
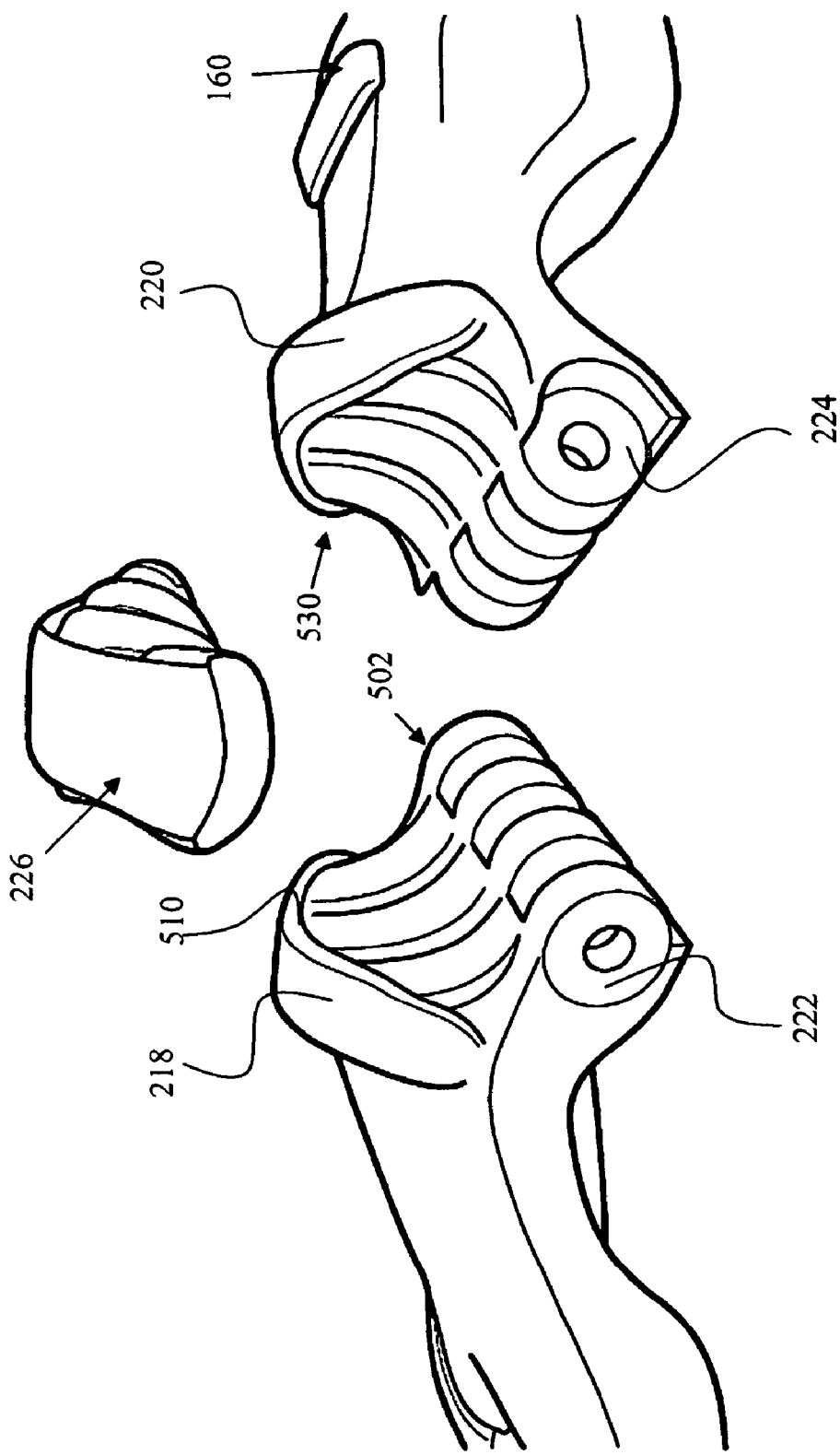
Figure 5D:
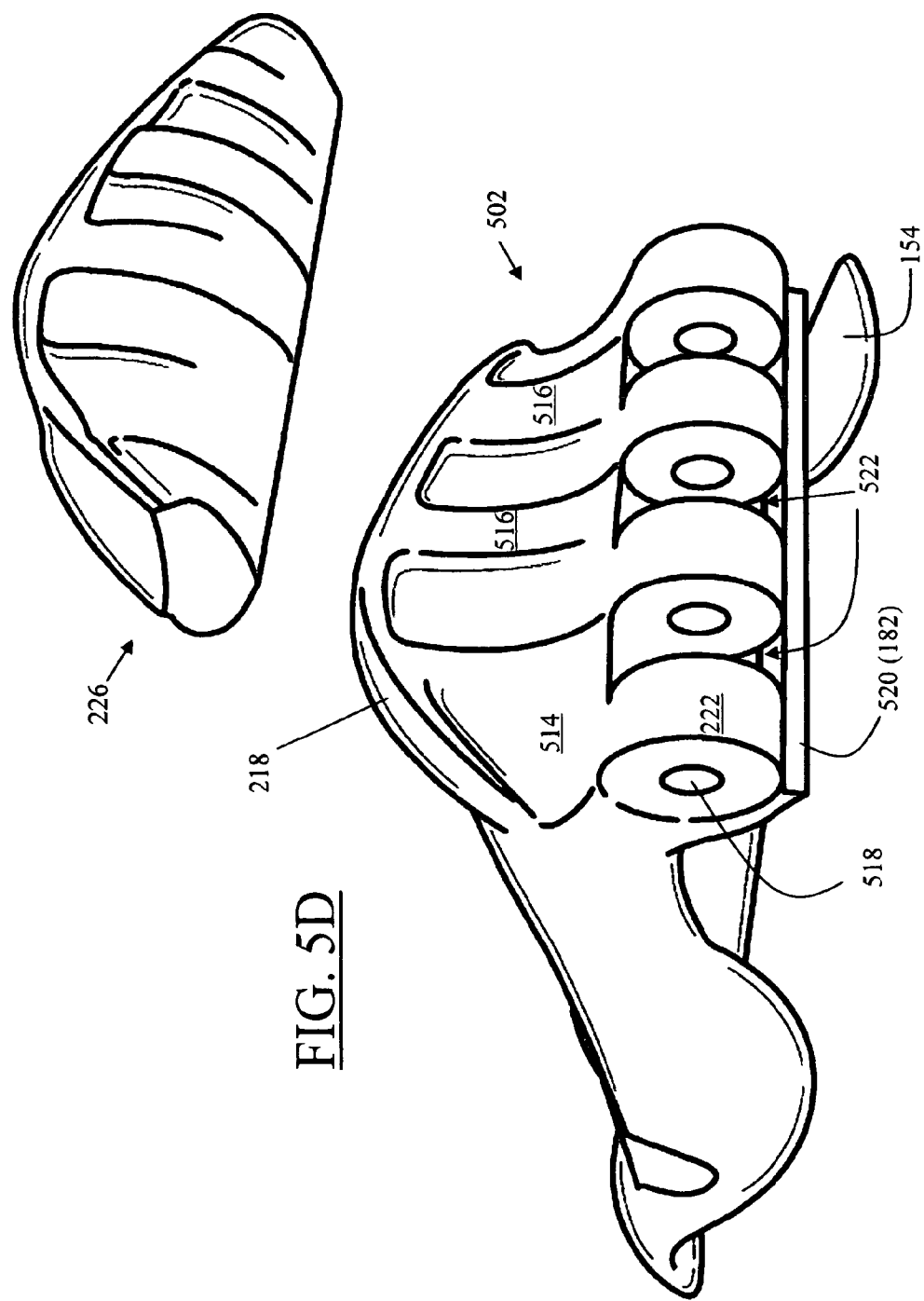
FIG. 5D is an exemplary exploded perspective view of the proximal end of the quaternary section of the fore foot of the prosthetic extremity of FIG. 1A.
Figure 6A:
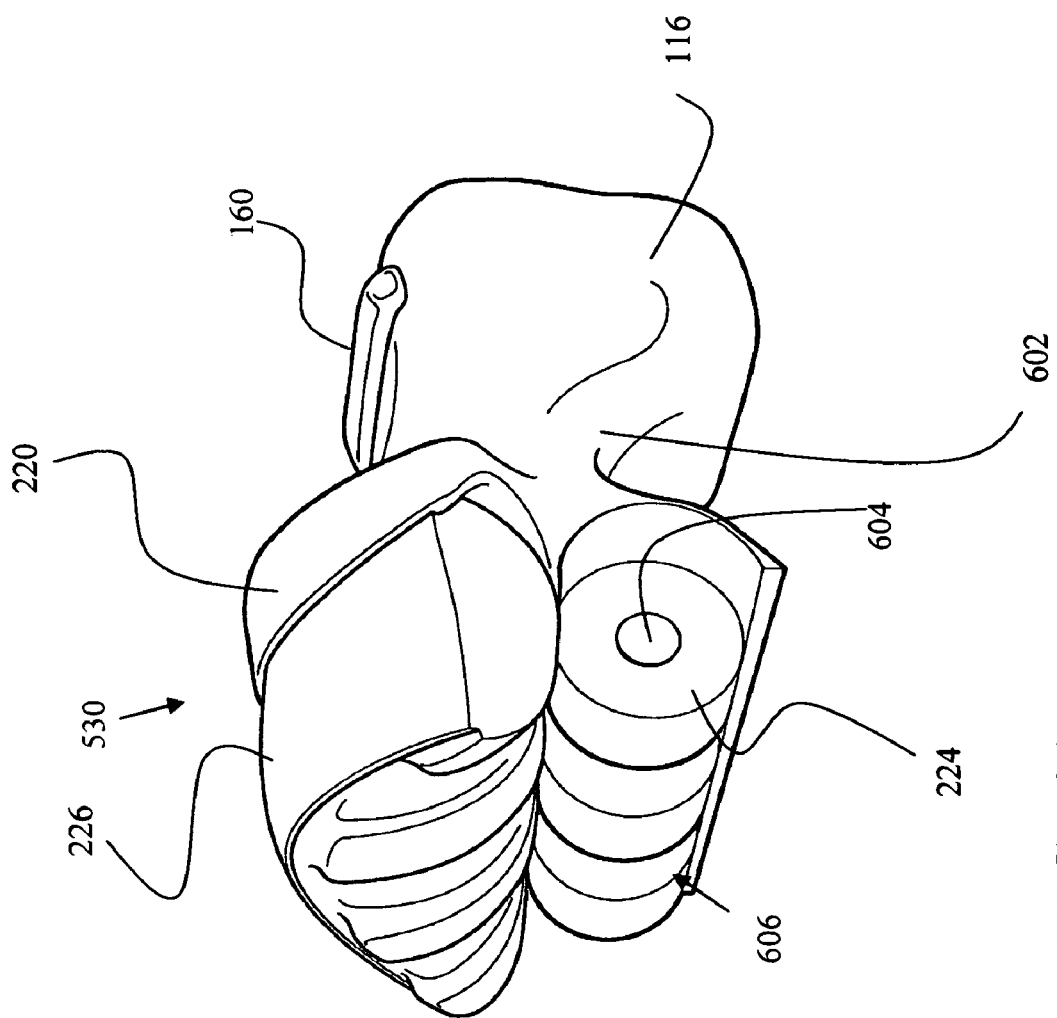
FIG. 6A is an exemplary perspective view of the proximal end of the heel of the prosthetic extremity of FIG. 1A.
Figure 6D:
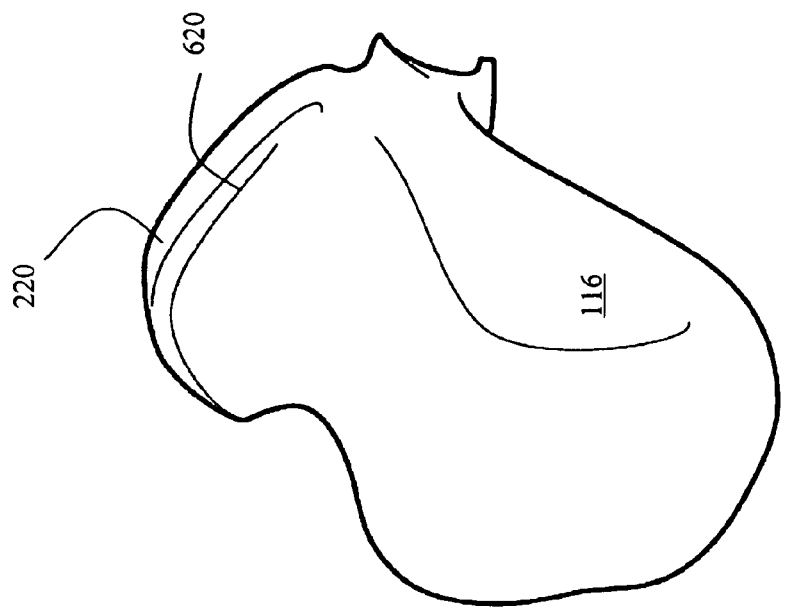
FIG. 6D is an exemplary perspective view of the distal end (posterior) of the heel of the prosthetic extremity of FIG. 1A.
Figure 6C:
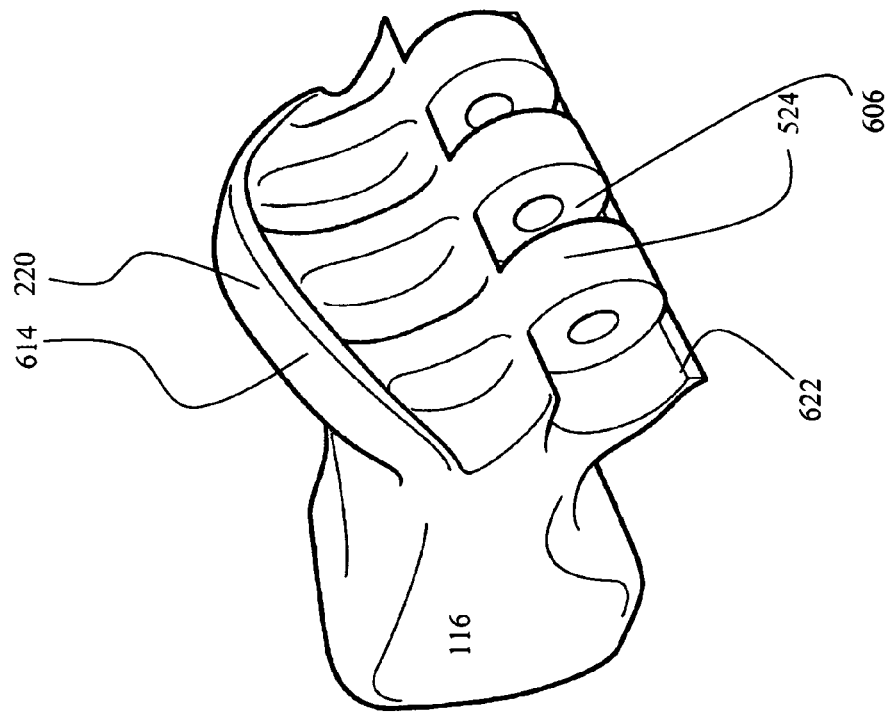
FIG. 6C is an exemplary perspective view of the proximal end of the heel of the prosthetic extremity of FIG. 1A without the third elastomer spring.

As best illustrated in FIGS. 7A to 7E, the third spring 226 is comprised of an elastomer with asymmetrical configuration having a varying axial length 702, a varying width 704, and a varying thickness 708. The elastomer spring 226 includes a top surface 710 that includes slightly convex section that is extended longitudinally, along the axial length 702 of the elastomer spring 226. The convex shape effects the manner by which the elastomer spring 150 counters applied forces. The slightly convex section top surface 710 includes lateral edge depressions 712 extending longitudinally, along the axial length 702 of the elastomer spring 226. The elastomer spring 226 further includes two lateral side surfaces 714 (FIG. 7D) and 716 (FIG. 7E) that extend longitudinally along the axial length 702 of the spring 226. The lateral side surfaces 714 and 716 include a plurality of notches 718 that are formed into the lateral side surfaces 714 and 716 of the elastomer spring 226. The notches 718 are aligned laterally along the axial length 702 of the elastomer spring 226, forming an alternating notch 718 and protuberance 720. Each notch of the plurality of notches 718 is comprised of a substantially smooth curved base, which protrude from the base, which form the two side walls of each notch 718, forming the smooth, curved protuberances 720. The lateral side surfaces 714 and 716 form a syncline shaped proximal a rounded bottom surface 722. As best illustrated in FIGS. 5A to 5C, the elastomer spring 226 with its plurality of notches 718 is positioned within the first and second sections 502 and 530 of the hinge biasing mechanism 202 such that each notch 718 is biased against a corresponding protrusion 516 and 612 on the first and second sections 502 and 530 of the hinge biasing mechanism 202. The asymmetrical elastomer spring 226 contacting the hinge biasing mechanism 202 and biasing it so that the hinge biasing mechanism 202 counter-balances compression and tensile forces exerted thereon, creating an incremental secondary articulations of the foot assembly 102. The two lateral edge depressions 712 securely abut the lip 510 and 614 of the hinge biasing mechanism 202.

Figure 8A:
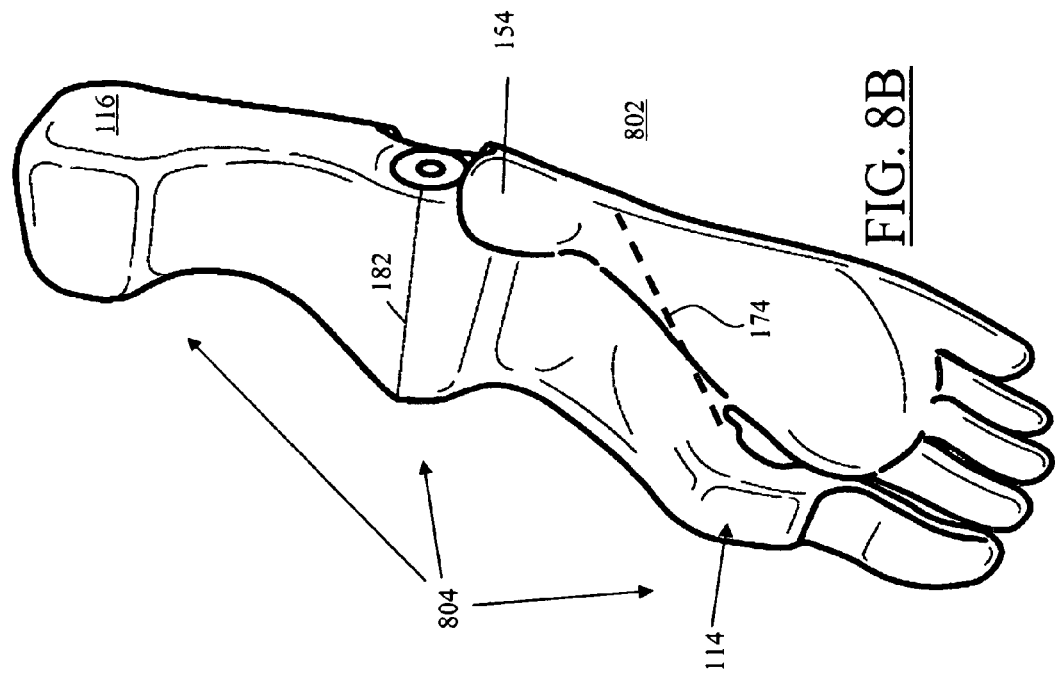
FIGS. 8A and 8B are exemplary perspective views of the plantar surface of the prosthetic extremity of FIG. 1A.
Figure 8B:
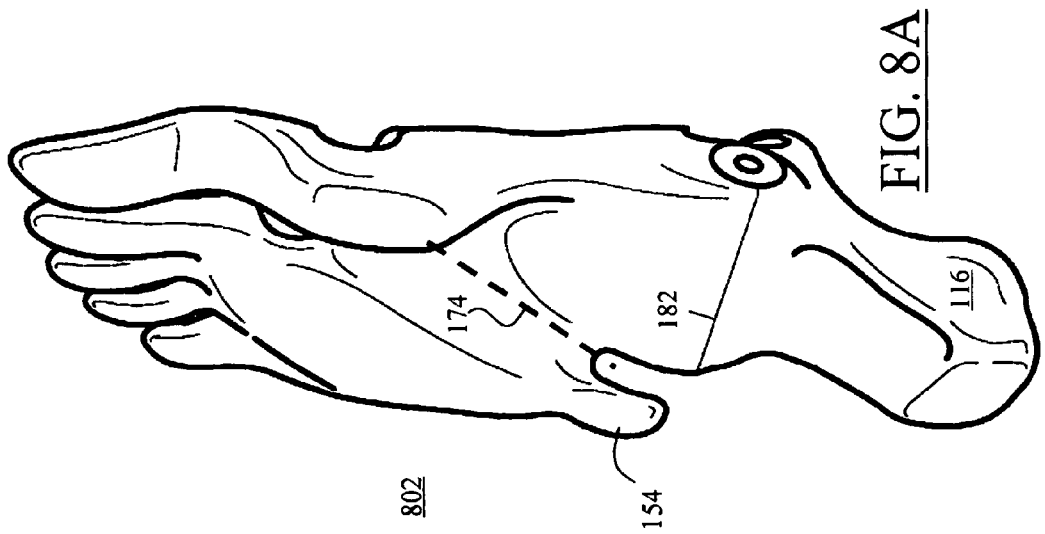
Figure 9A:
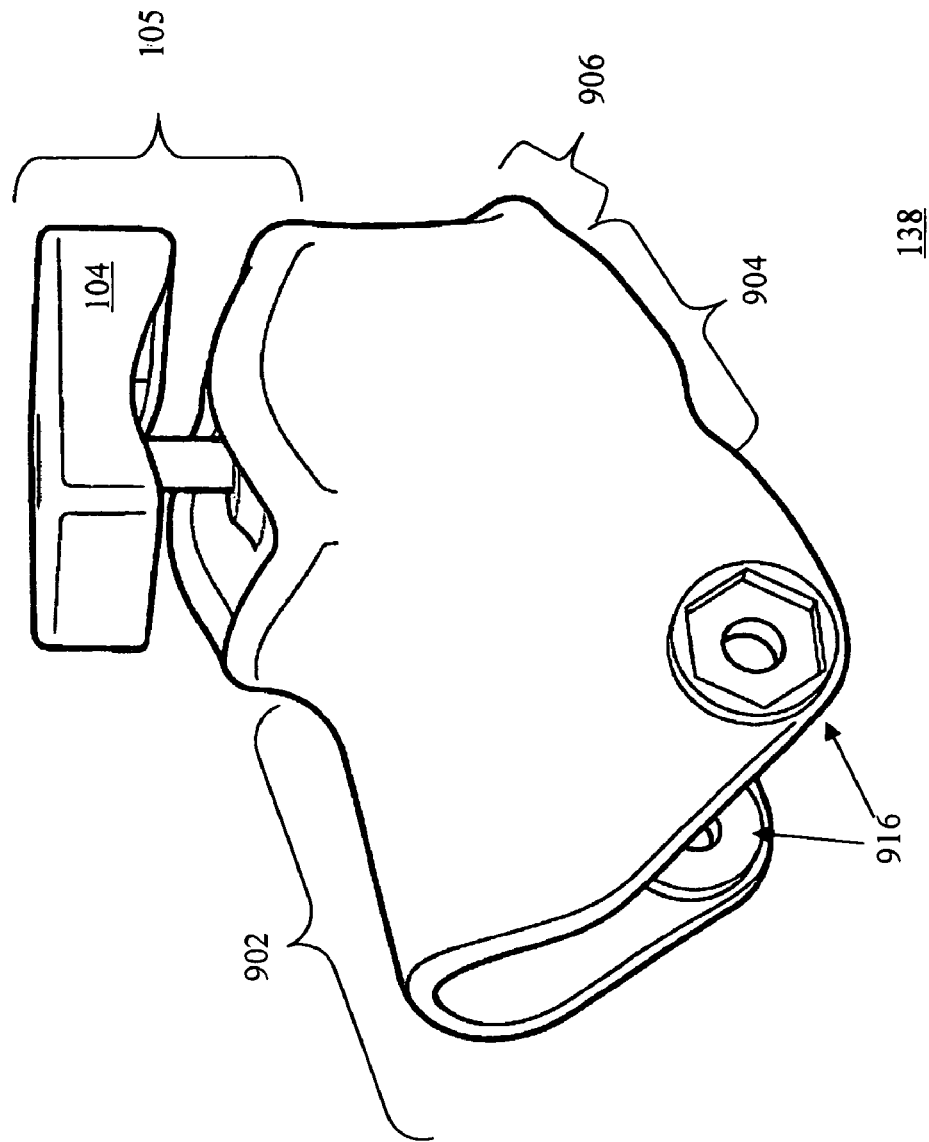
Figure 9B:
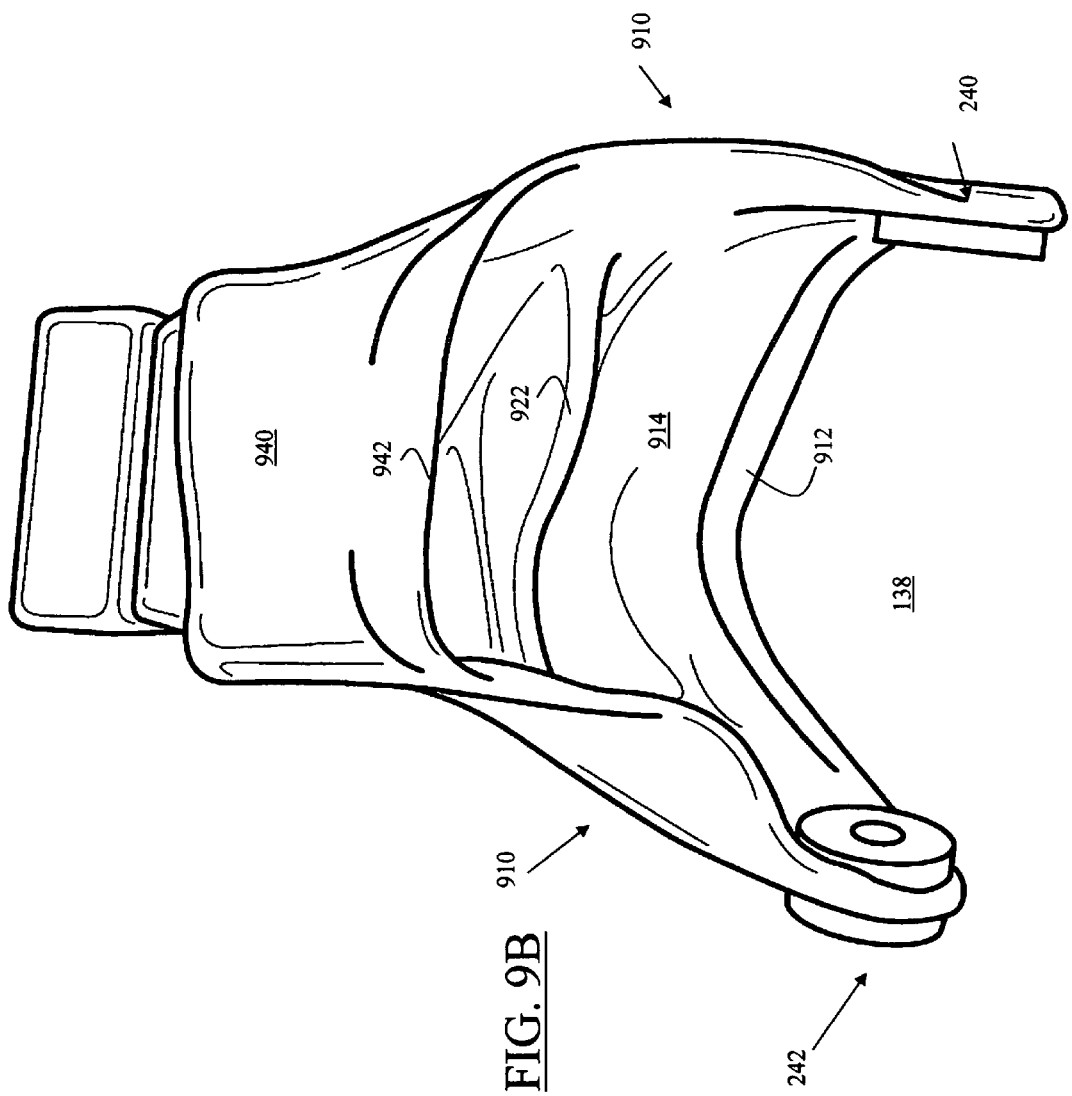
Figure 9D:
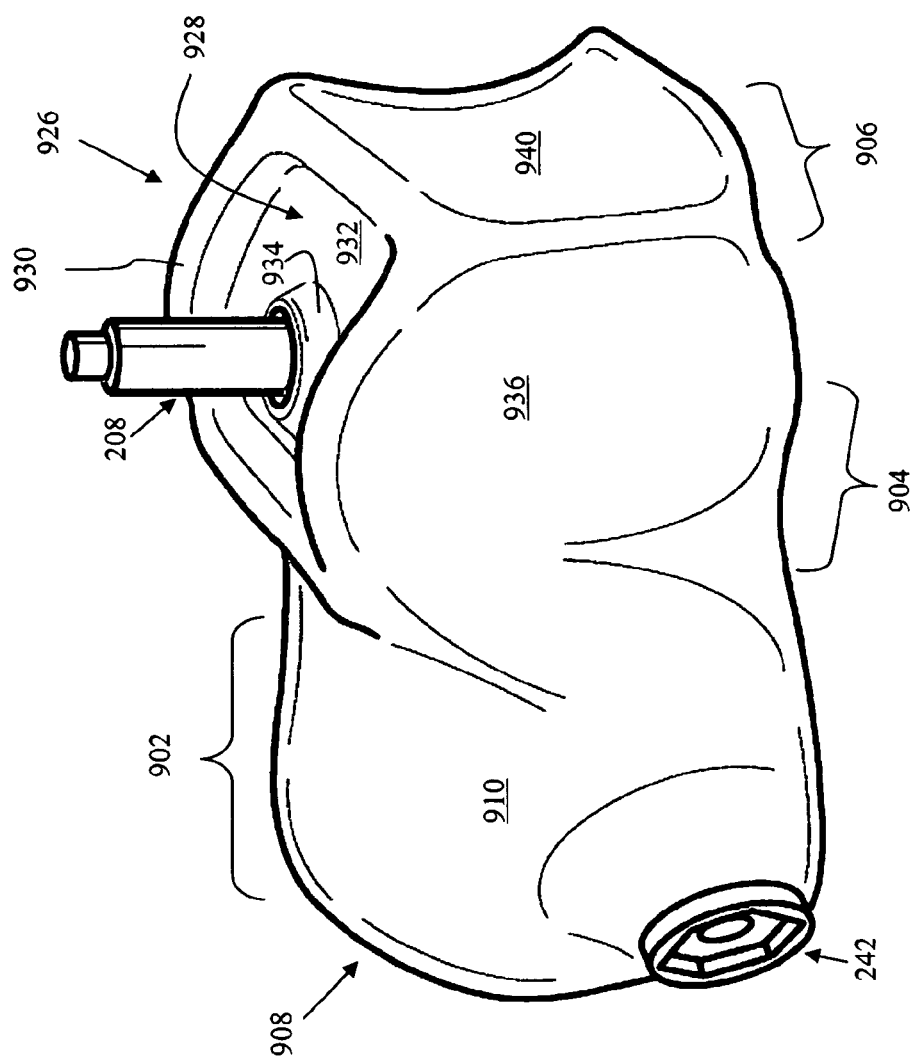
Figure 9E:
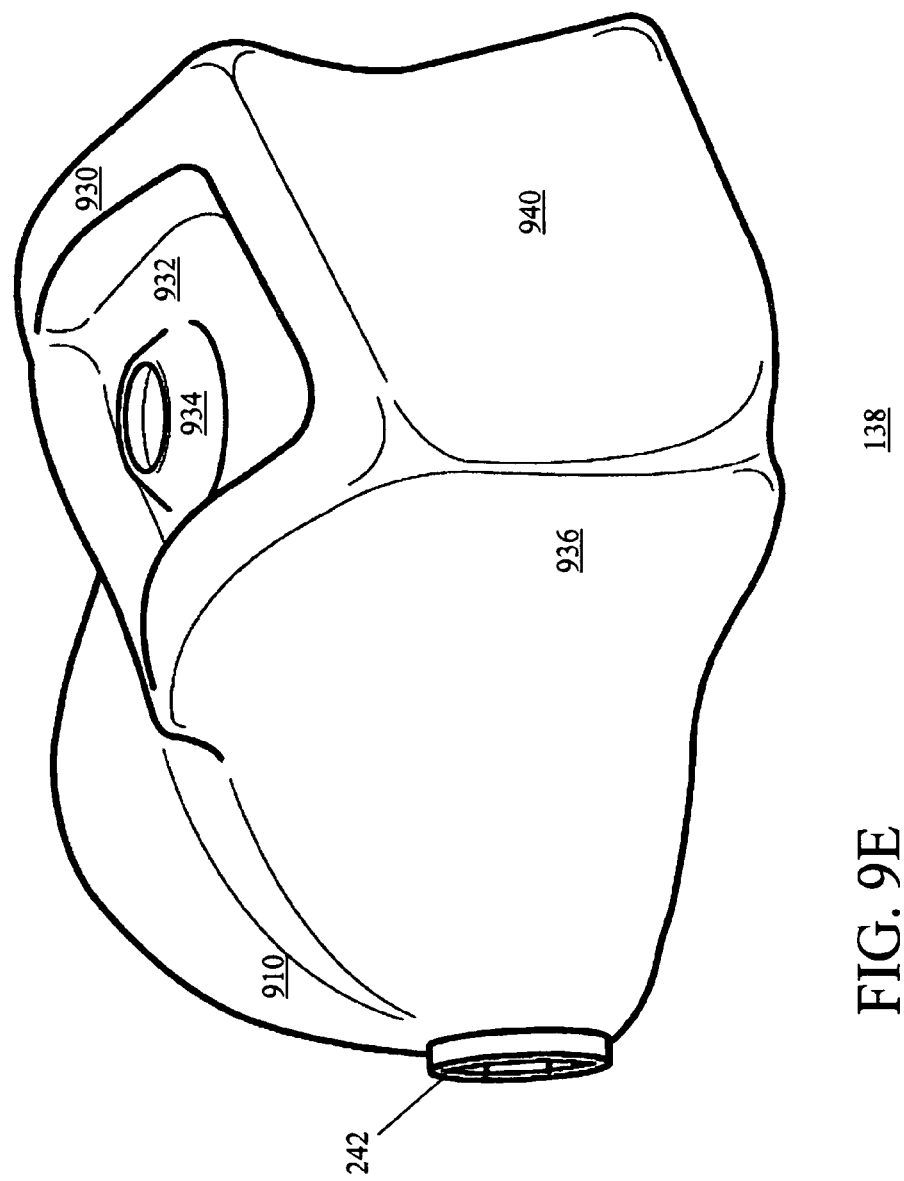
Figure 9F:
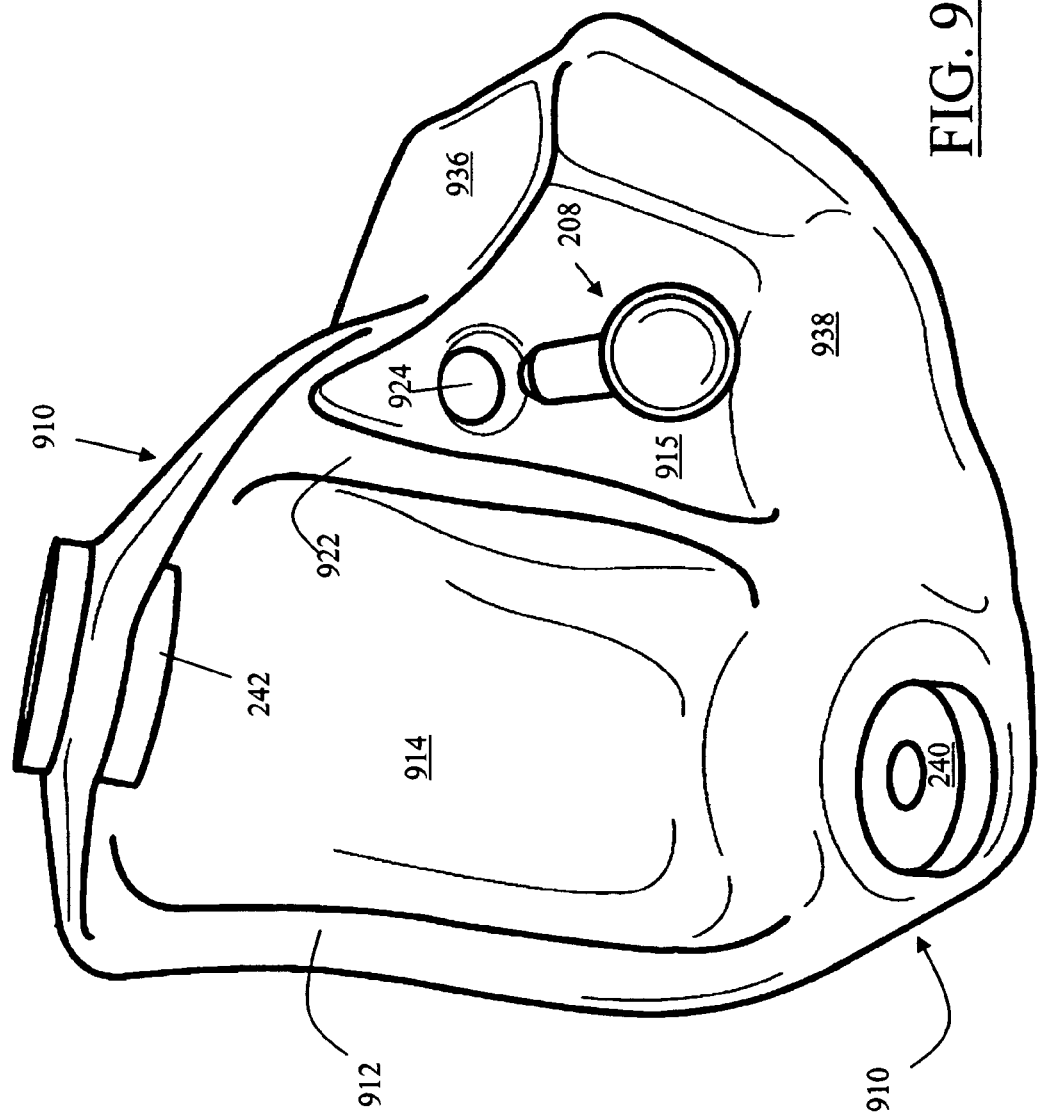
Figure 9G:
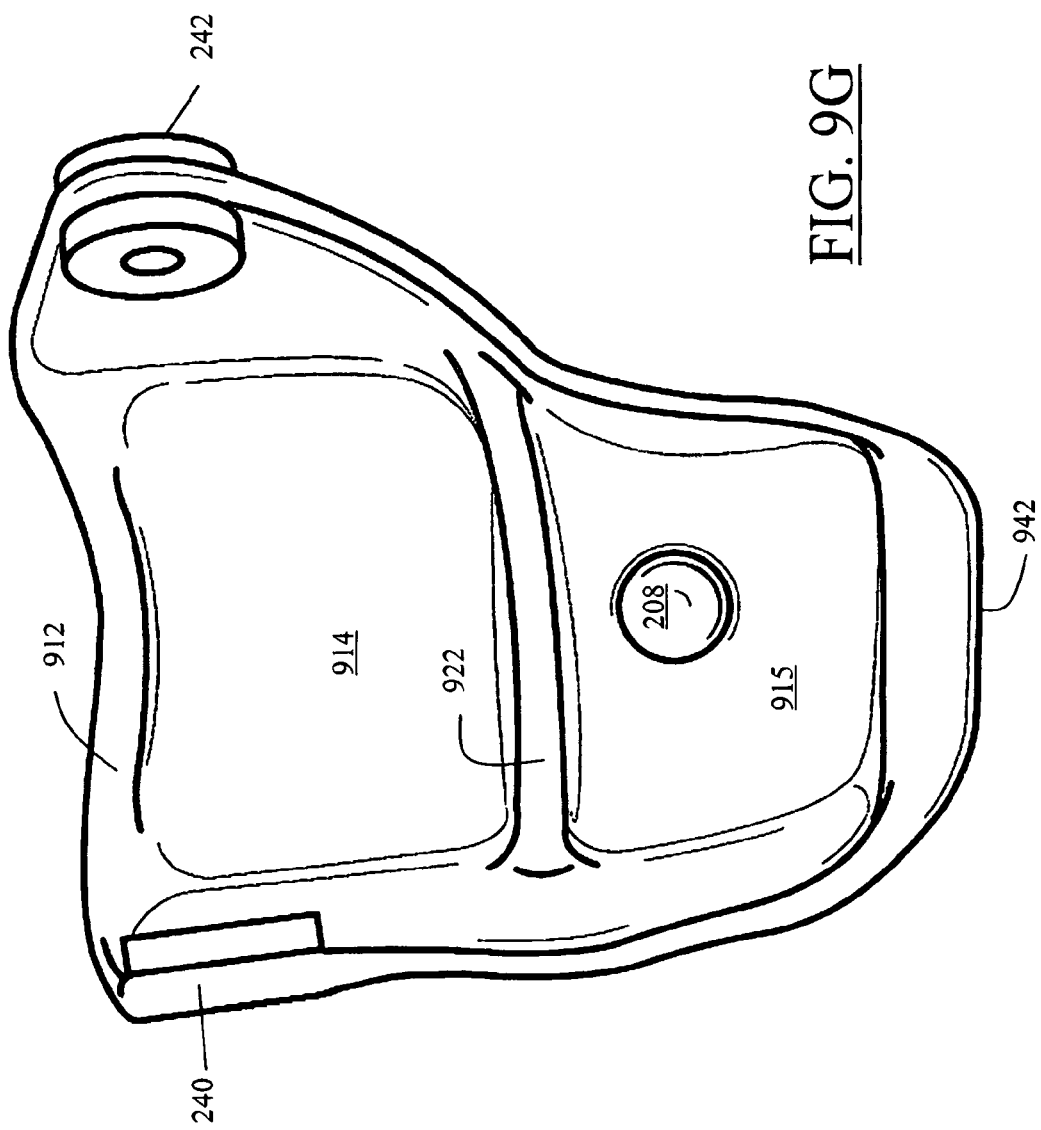

FIGS. 8A and 8B are exemplary perspective illustrations of the plantar surface of the foot assembly 102 in accordance with the present invention. As illustrated, the plantar surface 802 is asymmetrical, and includes a fore-foot planter surface, comprising a primary section configured as phalanges, a secondary section configured as metatarsal joints, a tertiary section configured as metatarsals, and a quaternary section for coupling the fore foot with the heel, arch suspension yoke, and the ankle assembly. Further included is a heel planter surface. As illustrated in FIG. 8B, the inner foot 804, from the plantar surface of the heel to the ball 114 of the foot assembly 102, is incurvate, forming the main arch 180. The first and second lower end stops 520 and 622 form the illustrated stop 182. Further, the tertiary articulation 177 is achieved by bending of the lower section of the metatarsal 176 about the axial line 174.

FIGS. 9A to 9G are exemplary perspective illustrations of the various views of the arch suspension yoke of the prosthetic extremity in accordance with the present invention. As illustrated, as with all individual components of the present invention, for example, the fore foot 136, the heel 116, the ankle 105, and the respective first, second, and third elastomer springs 150, 152, 226, ankle joint 106, including the damper 160, the arch suspension yoke 138 is also asymmetrical, and includes an asymmetrical anterior section 902, an asymmetrical medial section 904, and an asymmetrical posterior section 906.

The asymmetrical anterior section 902 includes a substantially saddled shaped dorsal surface 908 contiguous with asymmetrical anterior lateral walls 910. The walls 910 are not parallel to one another, and further, each individual wall is asymmetrical. The asymmetrical anterior section 902 further includes a first stop 912 integral with bottom surface 914 of a first distal end of the anterior section 902, limiting the secondary articulations of the fore foot 136 in the dorsiflexion and planiflexion motions. Further included is a main hinge coupler 916 for coupling the fore foot 136, the heel 116, and the arch suspension yoke 138 along an arch flex pivot axis 132. The main hinge 916 is comprised of a first main hinge coupler 240 facing an outer foot, which is positioned lower than a second main hinge coupler 242 facing an inner foot, with the first main hinge coupler 240 and the second hinge coupler 242 aligned along the arch flex pivot axis 132.

As further illustrated in FIGS. 9A to 9G, the asymmetrical medial section 904 of the arch suspension yoke 138 includes a second stop 922 integral with bottom surface 915 of a medial section 904, limiting the secondary articulations of the heel 116 in the dorsiflexion and planiflexion motions. Further included is a shaft aperture 924 axially aligned with a leg (not shown) for insertion of a ball joint shaft 208 for coupling of the arch suspension yoke 138 with the ankle assembly 105. A top surface 926 of the medial section 904 includes asymmetrical, substantially rectangular housing 928 formed from protruded perimeter edges 930, which house the ankle elastomer 106, with an asymmetrical interior bottom surface 932. The protruded perimeter edges 930 and the interior bottom surface 932 along an outer foot assembly is higher than the protruded perimeter edges 930 and the interior bottom surface 932 along an inner foot assembly, limiting and directing primary articulations. The top surface 926 further includes a dome wall 934 surrounding the shaft aperture 924, constituting the ball joint shaft capture. Medial lateral walls 936 and 938 are substantially vertically oriented with incurvate section on the inner foot assembly side, and substantially convex on the outer foot side.

As further illustrated in FIGS. 9A to 9G, the asymmetrical posterior section of the arch suspension yoke includes a posterior, vertically oriented wall 940 with incurvate at a midsection having a concaved portion that is substantially parallel with the transverse direction of the foot assembly 102. A third stop 942 integral with bottom surface of posterior section, limits and directs the secondary and tertiary articulations of the heel 116 when in contact with a heel damper elastomer 160.

As best illustrated in FIGS. 2A, 9A, 9C, 9D, 9F, 9G, and 10A to 10C, the ball joint shaft 208 is comprised of a bottom, substantially spherical ball that is integral with a substantially cylindrical elongated shaft with a threaded end, and edged top-end (in the form of an exemplary hexagon). As illustrated, the ball join shaft 208 is inserted through the shaft aperture 924, with the substantially spherical ball section thereof housed within the underside of the dome wall 934 surrounding the shaft aperture 924. The shaft section of the ball joint shaft 208 is further inserted through the aperture 1102 of the ankle joint 106 and a threaded shaft hole 1002 of the fastener element 104. The top of the ball joint shaft 208 is also threaded to be fixed within the threaded shaft hole 1002, and includes the exemplary hex top for adjusting tightness and preloading the elastomer spring 106.

Figure 10A:
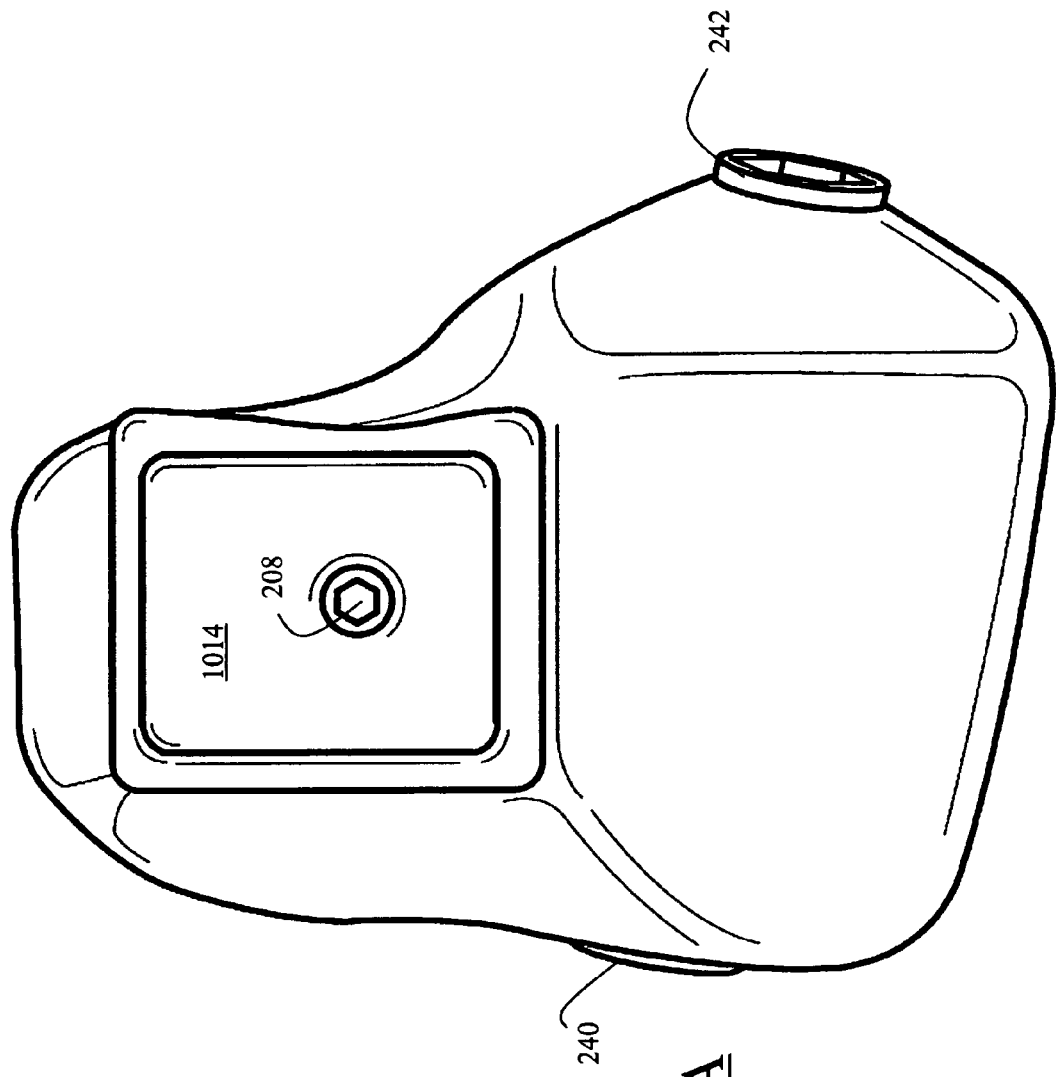
FIGS. 10A to 10C are exemplary perspective views of the ankle assembly of the prosthetic extremity of FIG. 1A.
Figure 10B:
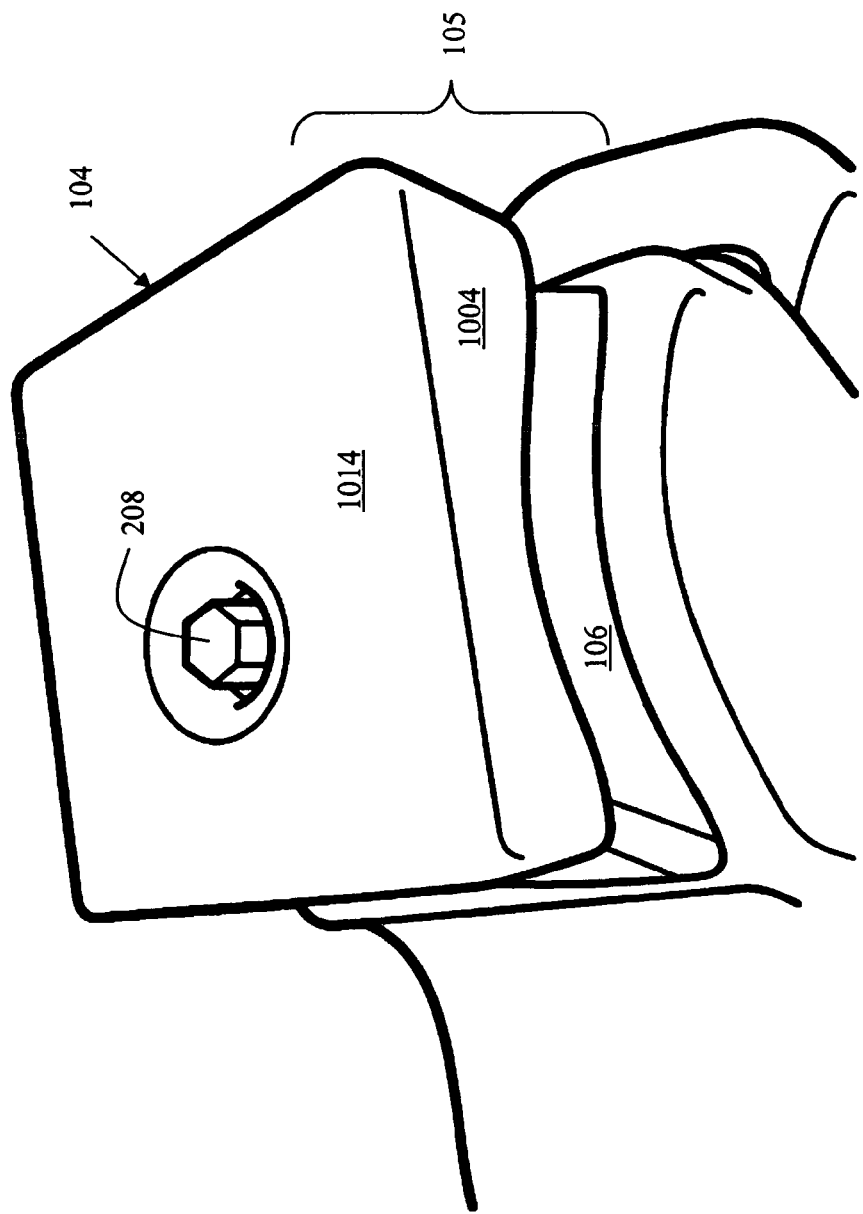
Figure 10C:
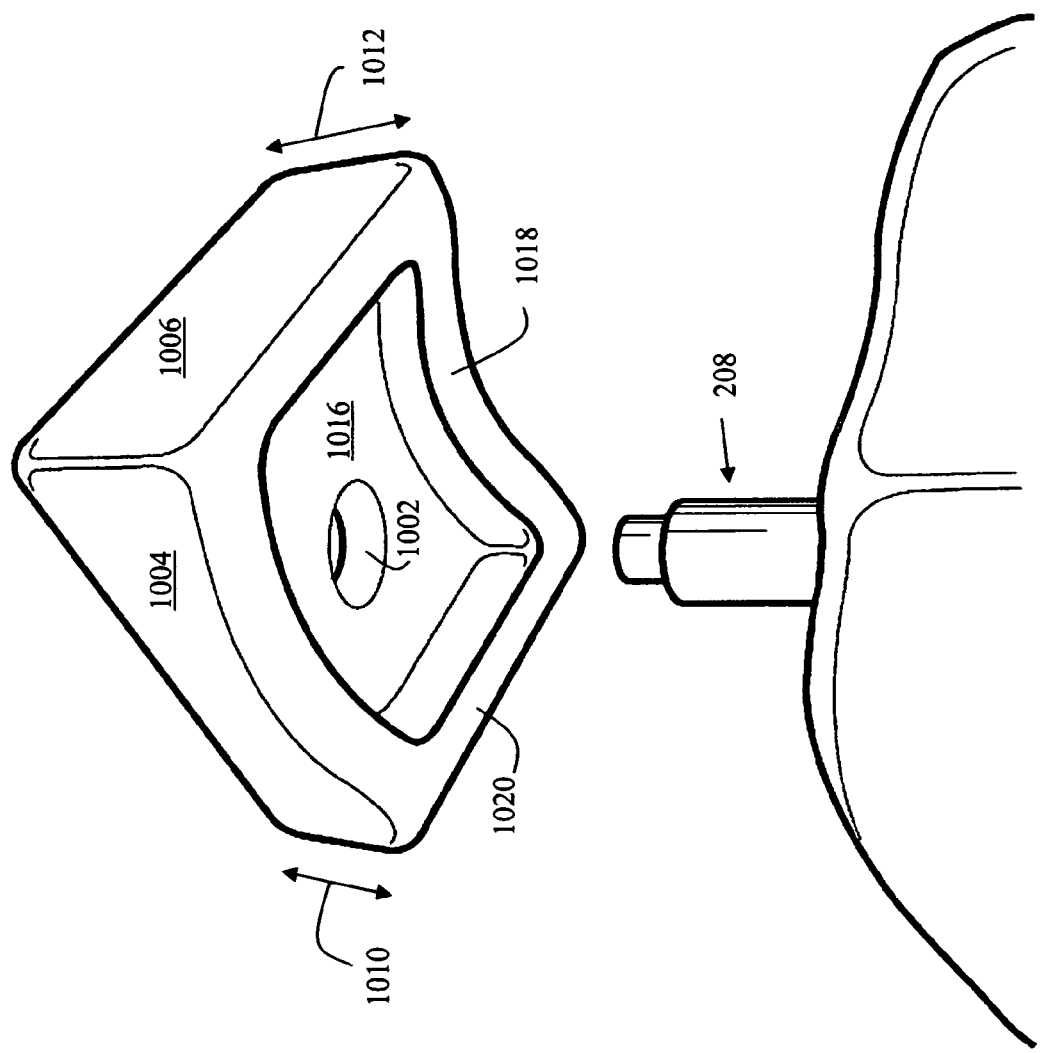

As best illustrated in the figures showing the ankle assembly 105, and in particular, FIGS. 10A to 10C, the fastener element 104 of the ankle assembly 105 is asymmetrical, having a threaded shaft hole 1002 axially aligned with the shaft aperture 924 of the arch suspension yoke 138 for insertion of the ball joint shaft 208 for coupling of the arch suspension yoke 138 with the ankle assembly 105. The fastener element 104 has a lateral perimeter that is configured substantially rectangular with a length 1004 that is substantially parallel with a length 108 of the foot assembly 102 and a width 1006 that is transverse the length 108, and an anterior height 1010 that is shorter than a posterior height 1012. Further included, is a substantially flat fixation surface 1014 for coupling with a leg (not shown). The bottom surface 1016 is a cavity for housing an ankle elastomer spring 106. The bottom surface rim 1018, protruded form the lateral perimeter and extending along the bottom surface perimeter, with a length side 1018 concaved and a width 1020 sides flat are inversely commensurate with the top surface 926 of a medial section 904 of the arch suspension yoke 138. As further illustrated in FIG. 10C, the top of the ball joint shaft 208 is also threaded to be fixed within the threaded shaft hole 1002, and includes the exemplary hex top for adjusting tightness and preloading the elastomer spring 106.

Figure 11A:
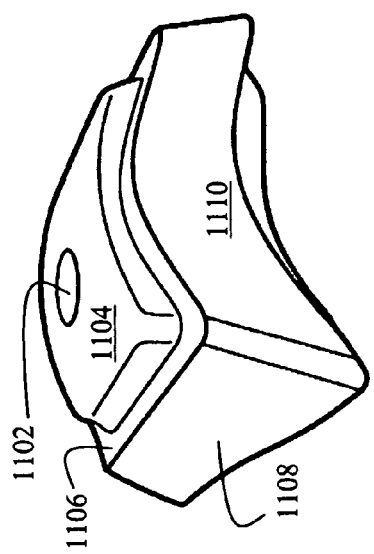
FIGS. 11A to 11G are exemplary perspective views of the fourth elastomer spring of the prosthetic extremity of FIG. 1A.
Figure 11C:
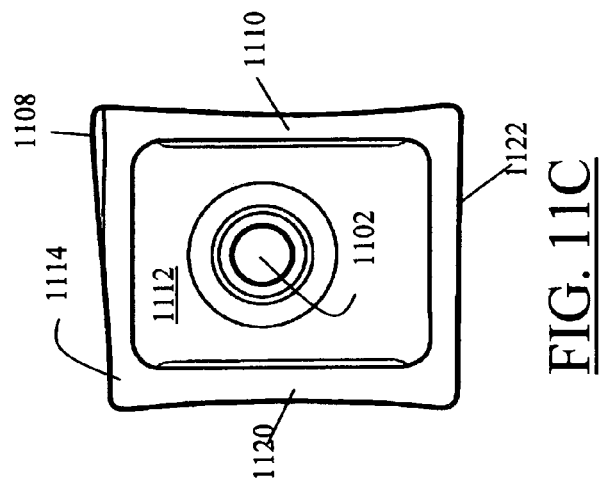
Figure 11B:
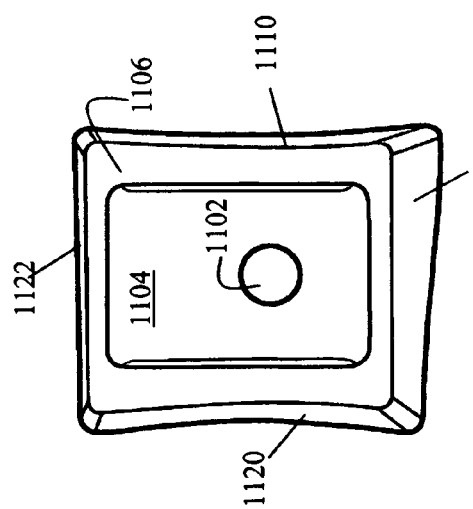
Figure 11D:
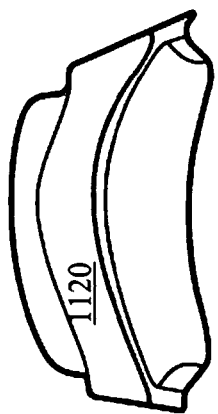
Figure 11E:
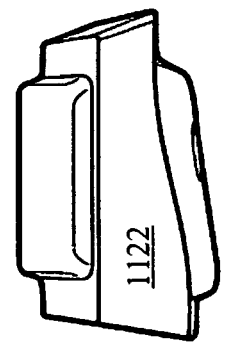
Figure 11F:
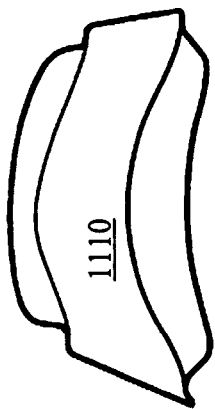
Figure 11G:
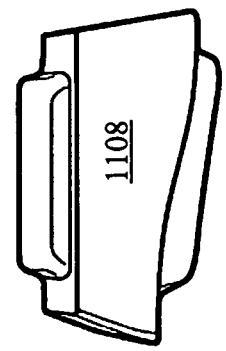

FIGS. 11A to 11G are exemplary illustrations of the various views of the asymmetrical ankle joint elastomer 106 of the prosthetic extremity in accordance with the present invention. As illustrated, the ankle joint elastomer 106, as with other components is asymmetrical, and is housed within the bottom surface 1016 of the fastener element 104, and the interior bottom surface 932 of the arch suspension yoke 138. The asymmetrical form of the ankle joint elastomer 106 is an indicative of the asymmetrical configuration of the top surface 926 of a medial, section 904 of the arch suspension yoke 138 and the fastener element 104. As illustrated, the ankle joint elastomer 106 includes an aperture 1102. The shaft section of the ball joint shaft 208 is further inserted through the aperture 1102 through which the ball joint shaft 208 is inserted. The top surface 1104 of the ankle joint 106 and its steps 1106 contacts the bottom surface 1016 and perimeters 1020 and 1018 of the fastener element 104, and the bottom surface 1104 of the ankle joint 106 contacts the bottom surface 932 of the top section 926 of the arch suspension yoke 138. The steps 1114 of the ankle joint 106 contact the perimeters 930 of the top section 926 of the arch suspension yoke 138. The various lateral sides illustrated in FIGS. 11D to 11G extend out from in between the top section 926 of the arch suspension yoke 138 and the fastener element 104. FIG. 11D is an exemplary illustration showing the wall 1110 of the ankle joint 106 from the inner (tibial) side of the foot, and FIG. 11E is wall 1120 facing the outer (fibular) side of the foot. FIG. 11F is wall 1108 facing the front and FIG. 11G is the wall 1122 facing the back.

FIGS. 12A and 12B represent the method by which the range of primary articulations in the inversion/eversion and dorseflixion/plantiflexion directions of the foot can be preset in relation to the fixation surface 1014 of the fastener element 104 of the ankle assembly 105. This can be achieved by adjusting the dimensions of the wall (1110, 1120, 1108, 1122) of the ankle elastomer spring 106. This allows the prosthetic foot assembly 102 in relation to the fastener element 104 to be preset in an orientation that matches, as closely as possible, the natural "hang" of the foot in relation to the leg, when the leg is perpendicular to the ground and the prosthetic foot assembly 102 is above the ground and at rest. This preset relationship between the leg and prosthetic foot assembly 102 is a vital part of the natural gait of the person and the correct transfer of force throughout the ankle and foot as the walk through is performed.

FIG. 12A represents an ankle and foot preset with an ankle elastomer 106 having specific wall dimensions (such as that shown in dashed circle 1202) such that when the foot is at rest on the ground, with no downward force, the plantar surface of the foot assembly 102 is substantially perpendicular to the leg. FIG. 12B represents an ankle and foot preset with an ankle elastomer 106 having specific wall dimensions (such as that shown in dashed circle 1204) such that the foot assembly 102 has a non-limiting, exemplary 4 degree downward tilt (planiflexion) and a non-limiting, exemplary 4 degree outside downward roll (eversion), both in relation to the vertical axis (the leg).

Although the invention has been described in considerable detail in language specific to structural features and or method acts, it is to be understood that the invention defined in the appended claims is not necessarily limited to the specific features or acts described. Rather, the specific features and acts are disclosed as preferred forms of implementing the claimed invention. Stated otherwise, it is to be understood that the phraseology and terminology employed herein, as well as the abstract, are for the purpose of description and should not be regarded as limiting. Therefore, while exemplary illustrative embodiments of the invention have been described, numerous variations and alternative embodiments will occur to those skilled in the art. For example, variations in size of the elastomers, leaf springs, and so on. Such variations and alternate embodiments are contemplated, and can be made without departing from the spirit and scope of the invention.

It should further be noted that throughout the entire disclosure, the labels such as left, right, front, back, top, bottom, forward, reverse, clockwise, counter clockwise, up, down, or other similar terms such as upper, lower, aft, fore, vertical, horizontal, oblique, proximal, distal, parallel, perpendicular, transverse, longitudinal, etc. have been used for convenience purposes only and are not intended to imply any particular fixed direction or orientation. Instead, they are used to reflect relative locations and/or directions/orientations between various portions of an object.

In addition, reference to "first," "second," "third," and etc. members throughout the disclosure (and in particular, claims) is not used to show a serial or numerical limitation but instead is used to distinguish or identify the various members of the group.

In addition, any element in a claim that does not explicitly state "means for" performing a specified function, or "step for" performing a specific function, is not to be interpreted as a "means" or "step" clause as specified in 35 U.S.C. Section 112, Paragraph 6. In particular, the use of "step of," "act of," "operation of," or "operational act of" in the claims herein is not intended to invoke the provisions of 35 U.S.C. 112, Paragraph 6.

What is claimed is:

1. A prosthetic foot and ankle, comprising:
an ankle assembly coupled with a foot assembly, with the ankle assembly enabling primary articulations of the foot;
the foot assembly having a plantar surface and a dorsal surface includes a heel coupled with a forefoot by an arch suspension yoke, with the arch suspension yoke enabling secondary articulations of the foot assembly;
the forefoot includes:
a primary section configured as phalanges;
a secondary section configured as metatarsal joints;
a tertiary section configured as metatarsals; and
a quaternary section for coupling the forefoot with the heel, arch suspension yoke, and the ankle assembly;
the secondary section of the forefoot includes:
a first biasing mechanism with a first axial length and a second biasing mechanism with a second axial length that is longer than the first axial length;
the first axial length is oriented substantially transverse the longitudinal axis of the foot assembly, and the second axial length is oriented at an angle $\psi$ to the longitudinal axis of the foot assembly;
the first and the second biasing mechanisms are substantially cylindrical;
the first biasing mechanism is positioned slightly posterior the second biasing mechanism, with the first and second biasing mechanisms having a center line axis that is slightly bent;
the first biasing mechanism and the second biasing mechanism comprising:
a substantially "C" shaped toe spring cavity for housing a spring, including a joint leaf spring at a bottom surface of the toe spring cavity;
the toe spring cavity includes:
an elongated canal with a plurality of flanges, the flanges are aligned laterally along an axial width of the toe spring cavity, forming an alternating protuberance and depression within the toe spring cavity;
dorsal, inner bottom surface of the toe spring cavity is smooth and concaved, with the plantar, outer surface substantially flat, forming the joint leaf spring;
the spring is comprised of:
an elastomer having an axial length, a width, and a thickness;
a top surface that includes a slightly convex section that is extended longitudinally, along the axial length of the spring;
the slightly convex section includes lateral edge depressions extending longitudinally, along the axial length of the spring;
two lateral side surfaces, extending longitudinally along the axial length of the spring;
the lateral side surfaces includes a plurality of notches that are formed into the lateral side surfaces of the spring;
the notches are aligned laterally along the axial length of the spring, forming an alternating notch and protuberance;
each notch of the plurality of notches is comprised of a substantially flat base, with the perpendicular protuberances forming two side walls of each notch; and
a bottom surface;
the spring having the plurality of notches, positioned laterally along an axial length of the spring, with each notch biased against a corresponding protrusion on the spring cavity;
the spring contacting the spring cavity and biasing the spring cavity so that the spring cavity counter-rotates about the center line axis of the first and the second biasing mechanisms.

2. The prosthetic foot and ankle as set forth in claim 1, wherein:
the primary articulations are comprised of motions of dorsiflexion and plantarflexion, inversion and eversion, and transverse rotation.

3. The prosthetic foot and ankle as set forth in claim 1, wherein:
the secondary articulations are comprised of an arch flex motion about an arch flex pivot axis, which enable forefoot proximal end and a heel proximal end to travel in a reciprocal arc defined by the arch flex pivot axis.

4. The prosthetic foot and ankle as set forth in claim 1 wherein:
the primary section of the forefoot includes individually separate:
a first toe, a second toe, a third toe, a fourth toe, and a fifth toe, with each toe comprising:
a single piece unit having dorsal and plantar surfaces with substantially flat toe distal end continued obliquely to a raised toe median section that ends at a toe proximal end, with the toe median section forming a toe leaf spring enabling individual, tertiary articulations of the first toe, the second toe, the third toe, the fourth toe, and the fifth toe.

5. The prosthetic foot and ankle as set forth in claim 4, wherein:
the primary section of the forefoot further includes an abbreviated interosseous space between the first toe and the second toe.

6. The prosthetic foot and ankle as set forth in claim 1, wherein:
the tertiary section configured as metatarsals, includes:
oblique, dorsal surface forming an asymmetrical convex configuration extending transversely, oriented parallel a width of the foot from an inner side of foot to an outer side of the foot;
a balancing protuberance in the outer side of the foot extending parallel along longitudinal axis of the foot proximal a first pivot axis, including a balancing leaf spring; and
a forefoot main arch at the inner side of the foot.

7. The prosthetic foot and ankle as set forth in claim 1, wherein:
the quaternary section includes a first section of a hinge biasing mechanism having a longitudinal axis oriented at an angle $\theta$ to the longitudinal axis of the foot assembly, and tilted down at an angle $\phi$ from an inner forefoot to the outer forefoot;
the first section of the hinge foot biasing mechanism further comprising:
forefoot hinge barrels, oriented transverse the longitudinal axis of the foot;
the forefoot hinge barrels are comprised of integrally circular, hollow sections forming a set of forefoot pivot knuckles of a main hinge;
the set of forefoot pivot knuckles are inserted and interlocked with a set of heel pivot knuckles, with the integrally circular, hollow sections of the set of forefoot pivot knuckles and the heel pivot knuckles aligned, through which a main pin is inserted coupling the set of forefoot pivot knuckles and the heel pivot knuckles, forming the main hinge;

the first section of the hinge biasing mechanism includes a first section wall, having a plurality of vertically oriented flanges with smooth, rounded surfaces that are aligned laterally along the first section wall;

the first section of the hinge biasing mechanism also includes a first section top having a length that extends longitudinally along an axial width of the foot assembly and has a width forming a first lip;

a first top surface of a spring includes a first lateral edge depression that securely abuts the first lip of the first section of the hinge biasing mechanism.

8. The prosthetic foot and ankle as set forth in claim 1, wherein:

the heel is comprised of:

a posterior heel section with part of the dorsal surface covered with a heel damper mechanism;

a heel arch; and a second section of a hinge biasing mechanism.

9. The prosthetic foot and ankle as set forth in claim 8, wherein:

the heel damper is comprised of an elastomer.

10. The prosthetic foot and ankle as set forth in claim 8, wherein:

the second section of a hinge biasing mechanism has a longitudinal axis oriented at an angle θ to the longitudinal axis of the foot assembly, and tilted down at an angle φ from an inner forefoot to an outer forefoot, and comprising:

heel hinge barrels, oriented transverse the longitudinal axis of the foot;

the heel hinge barrels are comprised of integrally circular, hollow sections forming a set of heel pivot knuckles of a main hinge;

the set of heel pivot knuckles are inserted and interlocked with a set of forefoot pivot knuckles, with the integrally circular, hollow sections of the set of forefoot pivot knuckles and the heel pivot knuckles aligned, through which a main pin is inserted coupling the set of forefoot pivot knuckles and the heel pivot knuckles, forming the main hinge;

the second section of the hinge biasing mechanism includes a second section wall, having a plurality of vertically oriented flanges with smooth, rounded surfaces that are aligned laterally along the second section wall;

the second section of the hinge biasing mechanism also includes a second section top having a length that extends longitudinally along an axial width of the foot assembly and has a width forming a second lip;

a first top surface of a spring includes a second lateral edge depression that securely abuts the second lip of the second section of the heel forefoot biasing mechanism.

11. The prosthetic foot and ankle as set forth in claim 1, wherein:

the arch suspension yoke includes:

an asymmetrical anterior section;

an asymmetrical medial section; and an asymmetrical posterior section.

12. The prosthetic foot and ankle as set forth in claim 11, wherein:

the asymmetrical anterior section includes:

a substantially saddle shaped dorsal surface with asymmetrical anterior lateral walls;

a first stop integral with bottom surface of a first distal end of the anterior section, limiting the secondary articulations of the forefoot in the dorsiflexion and planiflexion motions;

a main hinge coupler for coupling the forefoot, the heel and the arch suspension yoke along an arch flex pivot axis;

the main hinge is comprised of a first main hinge coupler facing an outer foot, which is positioned lower than a second main hinge coupler facing an inner foot, with the first main hinge coupler and the second hinge coupler aligned along the arch flex pivot axis.

13. The prosthetic foot and ankle as set forth in claim 11, wherein:

the asymmetrical medial section includes:

a second stop integral with bottom surface of a medial section, limiting the secondary articulations of the forefoot in the dorsiflexion and planiflexion motions;

a shaft aperture axially aligned with a leg for insertion of a ball joint shaft for coupling of the arch suspension yoke with the ankle assembly;

a top surface of the medial section includes asymmetrical, substantially rectangular housing formed from protruded perimeter edges, which house an ankle elastomer, with an asymmetrical interior bottom surface;

the protruded perimeter edges and the interior bottom surface along an outer foot assembly is higher than the protruded perimeter edges and the interior bottom surface along an inner foot assembly, limiting and directing primary articulations;

the top surface further includes a dome wall surrounding the shaft aperture, constituting a ball joint shaft aperture;

medial lateral walls include substantially vertically oriented incurvate section on the inner foot assembly side, and substantially convex on the outer foot side.

14. The prosthetic foot and ankle as set forth in claim 11, wherein:

the asymmetrical posterior section includes:

a posterior, vertically oriented wall with incurvate at a mid-section having concaved portion that is substantially parallel with the transverse direction of the foot;

a third stop integral with bottom surface of posterior section, limiting the secondary articulation and a tertiary articulation of the heel when in contact with a heel damper elastomer.

15. The prosthetic foot and ankle as set forth in claim 1, wherein:

the ankle assembly is comprised of:

an asymmetrical fastener element having a threaded shaft hole axially aligned with a shaft aperture of the arch suspension yoke for insertion of a threaded ball joint shaft for coupling of the arch suspension yoke with the fastener element to form the ankle assembly, and for preloading an ankle elastomer;

the asymmetrical fastener element having:

a lateral perimeter that is configured substantially rectangular with a length that is substantially parallel with a length of the foot assembly and a width that is transverse the length, and an anterior height that is shorter than a posterior height;

a substantially flat fixation surface;

a bottom surface cavity for housing an ankle spring;

bottom surface rim, protruded from the lateral perimeter and extending along a bottom surface perimeter, with a length side concaved and a width sides flat, inversely commensurate with a top surface of a medial section of the arch suspension yoke.

16. The prosthetic foot and ankle as set forth in claim 1, wherein:
   the plantar surface of the foot assembly includes:
   a forefoot planter surface, comprising:
   a primary section configured as phalanges;
   a secondary section configures as metatarsal joints;
   a tertiary section configured as metatarsals; and
   a quaternary section for coupling the forefoot with the heel, arch suspension yoke, and the ankle assembly; and
   a heel planter surface comprising:
   a second section of a hinge biasing mechanism;
   a heel arch; and
   posterior planter surface of the heel.

17. The prosthetic foot and ankle as set forth in claim 1, further including:
   a ball joint shaft that couples the arch suspension yoke with a fastener element, forming the ankle assembly.

18. The prosthetic foot and ankle as set forth in claim 15, wherein:
   an ankle elastomer configuration presets an orientation of the foot assembly, and limits a range of primary articulations thereof, both in relation to a vertical axis.

* * * * *